(12) United States Patent
Nirogi et al.

(10) Patent No.: US 11,278,530 B2
(45) Date of Patent: Mar. 22, 2022

(54) POLYCYCLIC AMIDES AS MUSCARINIC M1 RECEPTOR POSITIVE ALLOSTERIC MODULATORS

(71) Applicant: SUVEN LIFE SCIENCES LIMITED, Hyderabad-Telangana (IN)

(72) Inventors: Ramakrishna Nirogi, Hyderabad (IN); Abdul Rasheed Mohammed, Hyderabad (IN); Anil Karbhari Shinde, Hyderabad (IN); Shankar Reddy Gagginapally, Hyderabad (IN); Durga Malleshwari Kancharla, Hyderabad (IN); Santosh Kumar Pandey, Hyderabad (IN); Renny Abraham, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 16/755,864

(22) PCT Filed: Oct. 26, 2018

(86) PCT No.: PCT/IB2018/058372
§ 371 (c)(1),
(2) Date: Apr. 13, 2020

(87) PCT Pub. No.: WO2019/082140
PCT Pub. Date: May 2, 2019

(65) Prior Publication Data
US 2020/0297703 A1    Sep. 24, 2020

(30) Foreign Application Priority Data
Oct. 27, 2017   (IN) .............................. 201741038173

(51) Int. Cl.
| | | |
|---|---|---|
| *A61K 31/437* | (2006.01) | |
| *A61P 25/28* | (2006.01) | |
| *A61K 31/13* | (2006.01) | |
| *A61K 31/27* | (2006.01) | |
| *A61K 31/4155* | (2006.01) | |
| *A61K 31/4184* | (2006.01) | |

(Continued)

(52) U.S. Cl.
CPC ............ *A61K 31/437* (2013.01); *A61K 31/13* (2013.01); *A61K 31/27* (2013.01); *A61K 31/4155* (2013.01); *A61K 31/4184* (2013.01); *A61K 31/427* (2013.01); *A61K 31/445* (2013.01); *A61K 31/473* (2013.01); *A61K 31/4709* (2013.01); *A61K 31/538* (2013.01); *A61K 31/55* (2013.01); *A61P 25/28* (2018.01); *C07D 215/48* (2013.01); *C07D 235/04* (2013.01); *C07D 401/10* (2013.01); *C07D 403/10* (2013.01); *C07D 405/10* (2013.01); *C07D 405/14* (2013.01); *C07D 413/10* (2013.01); *C07D 417/10* (2013.01); *C07D 417/14* (2013.01); *C07D 471/04* (2013.01)

(58) Field of Classification Search
CPC .. C07D 215/48; C07D 235/04; C07D 401/10; C07D 403/10; C07D 405/10; C07D 405/14; C07D 413/10; C07D 417/10; C07D 417/14; C07D 471/04; A61K 31/437; A61K 31/13; A61K 31/27; A61K 31/4155; A61K 31/4184; A61K 31/427; A61K 31/445; A61K 31/4709; A61K 31/473; A61K 31/538; A61K 31/55; A61P 25/28

See application file for complete search history.

(56) References Cited

U.S. PATENT DOCUMENTS

| | | | | |
|---|---|---|---|---|
| 2012/0232076 A1* | 9/2012 | Kuduk | ................. | C07D 221/02 514/233.2 |
| 2013/0059860 A1* | 3/2013 | Beshore | ................. | A61P 25/20 514/254.05 |

(Continued)

FOREIGN PATENT DOCUMENTS

| | | | |
|---|---|---|---|
| WO | 2011/084368 A1 | 7/2011 | |
| WO | WO-2011149801 A1 * | 12/2011 | ............. A61P 25/18 |

(Continued)

OTHER PUBLICATIONS

European Patent Office, International Search Report, PCT/IB2018/058372, dated Jan. 8, 2019, Rijswijk, Netherlands.

(Continued)

*Primary Examiner* — Daniel R Carcanague
(74) *Attorney, Agent, or Firm* — IpHorgan Ltd.

(57) ABSTRACT

The present invention relates to compounds of formula (I), or their isotopic forms, stereoisomers, tautomers or pharmaceutically acceptable salt (s) thereof as muscarinic M1 receptor positive allosteric modulators (M1 PAMs). The present invention describes the preparation, pharmaceutical composition and the use of compound formula (I).

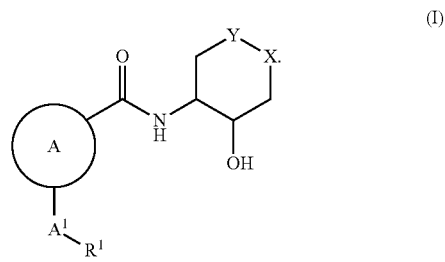

(I)

19 Claims, 1 Drawing Sheet

(51) Int. Cl.
*A61K 31/427* (2006.01)
*A61K 31/445* (2006.01)
*A61K 31/4709* (2006.01)
*A61K 31/473* (2006.01)
*A61K 31/538* (2006.01)
*A61K 31/55* (2006.01)
*C07D 215/48* (2006.01)
*C07D 235/04* (2006.01)
*C07D 401/10* (2006.01)
*C07D 403/10* (2006.01)
*C07D 405/10* (2006.01)
*C07D 405/14* (2006.01)
*C07D 413/10* (2006.01)
*C07D 417/10* (2006.01)
*C07D 417/14* (2006.01)
*C07D 471/04* (2006.01)

(56) References Cited

U.S. PATENT DOCUMENTS

| | | | | |
|---|---|---|---|---|
| 2013/0090352 A1* | 4/2013 | Gilbert | ............... | A61P 25/00 514/300 |
| 2015/0094328 A1* | 4/2015 | Payne | ............... | A61P 25/00 514/300 |
| 2015/0126487 A1* | 5/2015 | Sakamoto | ............ | C07D 405/12 514/210.18 |
| 2016/0194321 A1* | 7/2016 | Ballard | ............... | C07D 471/04 514/300 |
| 2016/0326144 A1* | 11/2016 | Groebkezbinden | .. | C07D 213/56 |
| 2017/0022173 A1* | 1/2017 | Lindsley | ............. | C07D 413/14 |
| 2018/0155302 A1* | 6/2018 | Nirogi | ............... | C07D 413/12 |
| 2018/0244655 A1* | 8/2018 | Nirogi | ............... | C07D 401/12 |
| 2019/0083467 A1* | 3/2019 | Ogino | ............... | A61K 31/4192 |
| 2019/0343812 A1* | 11/2019 | Nirogi | ............... | A61K 31/27 |
| 2020/0024275 A1* | 1/2020 | Lindsley | ............. | C07D 471/04 |
| 2020/0131159 A1* | 4/2020 | Lindsley | ............. | C07D 401/10 |
| 2020/0131180 A1* | 4/2020 | Lindsley | ............. | C07D 471/04 |
| 2020/0237761 A1* | 7/2020 | Nirogi | ............... | A61P 25/28 |
| 2021/0139491 A1* | 5/2021 | Takami | ............. | A61K 31/4355 |

FOREIGN PATENT DOCUMENTS

| | | | |
|---|---|---|---|
| WO | 2015/028483 | 3/2015 | |
| WO | 2016/009297 A1 | 1/2016 | |
| WO | 2016/198937 | 12/2016 | |
| WO | 2017/042643 | 3/2017 | |
| WO | 2017/123482 | 7/2017 | |
| WO | WO-2017123482 A1 * | 7/2017 | ........... C07D 401/06 |
| WO | 2017/143041 | 8/2017 | |
| WO | 2017/143041 A1 | 8/2017 | |
| WO | 2017/155050 A1 | 9/2017 | |
| WO | 2017/155816 | 9/2017 | |
| WO | WO-2017155816 A1 * | 9/2017 | ........... C07D 401/14 |
| WO | 2019/077517 | 4/2019 | |
| WO | WO-2020079606 A1 * | 4/2020 | ............. A61P 25/00 |

OTHER PUBLICATIONS

European Patent Office, Written Opinion of the International Searching Authority, PCT/IB2018/058372, dated Jan. 8, 2019, Berlin, Germany.
The International Bureau of WIPO, International Preliminary Report on Patentability, PCT/IB2018/058372, dated Apr. 28, 2020, Geneva, Switzerland.

* cited by examiner

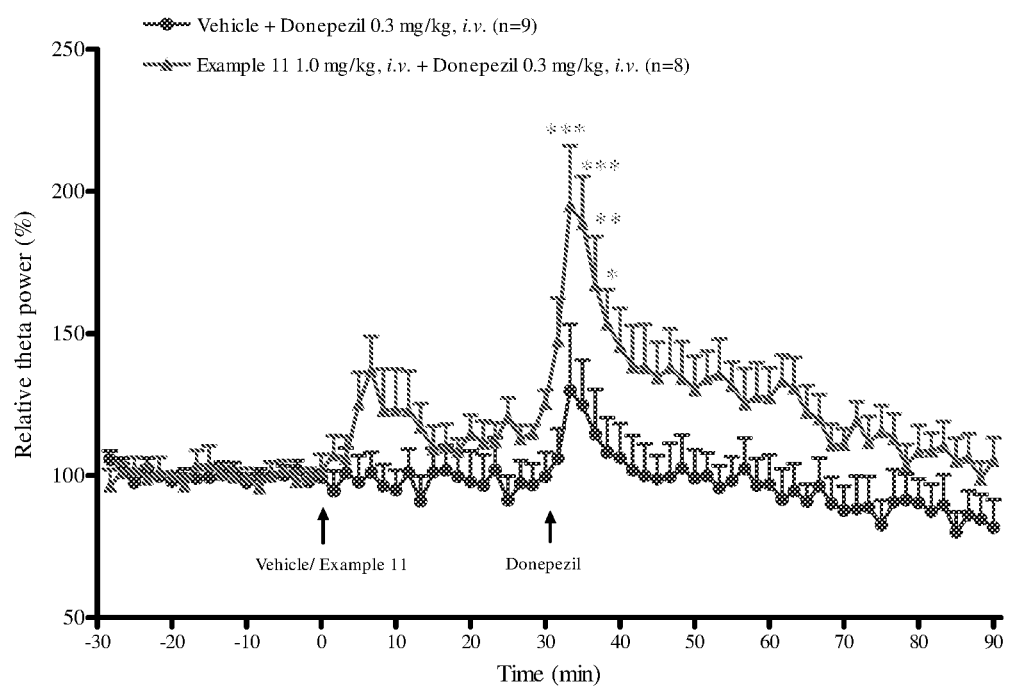

POLYCYCLIC AMIDES AS MUSCARINIC M1 RECEPTOR POSITIVE ALLOSTERIC MODULATORS

CROSS REFERENCE TO RELATED APPLICATIONS

This application is a national stage completion application of PCT Application No. PCT/IB2018/058372, filed Oct. 26, 2018, and claims priority from India Application No. 201741038173, filed Oct. 27, 2017. Each of these applications is incorporated by reference herein in its entirety.

FIELD OF INVENTION

The present invention relates to compounds of formula (I), or their isotopic forms, stereoisomers, or pharmaceutically acceptable salts as muscarinic M1 receptor positive allosteric modulators (M1 PAMs). The present invention also describes method of making such compounds, pharmaceutical compositions comprising such compounds and their use.

BACKGROUND OF THE INVENTION

Muscarinic acetylcholine receptors (mAChRs) which belong to the class A family of G protein-coupled receptors (GPCRs), are widely expressed throughout the body. Five subtypes termed M1 through M5 that respond to the endogenous neurotransmitter acetylcholine (ACh) has been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The M1 muscarinic receptor is predominantly expressed in the brain regions such as cortex, hippocampus and amygdala which involved in cognition, and therefore selective activation of the M1 receptor would be expected to boost cognitive performance (*Annals of Neurology*, 2003, 54, 144-146).

Xanomeline, a muscarinic acetylcholine receptor agonist with reasonable selectivity for the M1 and M4 subtypes, produced significant effects on cognition in a clinical Alzheimer's disease (AD) trial (*Alzheimer Disease and Associated Disorders*, 1998, 12(4), 304-312) although gastrointestinal side effects led to a high dropout rate in clinical trials. There is a high degree of conservation between muscarinic receptor subtypes at their orthosteric acetylcholine ligand binding sites which makes it difficult to identify a M1 selective agonist.

To circumvent this issue of selectivity and safety, an alternative approach consists of developing M1 PAMs that act at the less conserved allosteric binding site. Merck reported the development of M1 PAM, PQCA (1-{[4-cyano-4-(pyridine-2-yl)piperidin-1-yl]methyl}-4-oxo-4H-quinolizine-3-carboxylic acid). This compound is highly selective for M1 over the other muscarinic receptor subtypes and found to be efficacious in several preclinical models of cognition (*Psychopharmacology*, 2013, 225(1), 21-30) with no gastrointestinal side effects at doses equal to or less than a fivefold margin from the minimum effective dose required to improve cognition. In preclinical studies it was demonstrated that M1 activation increases neurotransmitter acetylcholine concentration in brain. Moreover, the M1 activation has potential as disease-modifying therapy for AD by both shifting the APP processing towards the non-amyloidogenic α-secretase pathway and by decreasing the tau hyper-phosphorylation. Positive allosteric modulators at M1 receptor have demonstrated to increase the generation of sAPPα in-vitro (*The Journal of Neuroscience*, 2009, 29, 14271-14286). Therefore, M1 PAMs provide an approach to target both symptomatic and disease-modifying treatment of cognitive deficits in AD and schizophrenia.

PCT patent application publications, WO2017155050, WO2017143041, WO2017123482 and WO2011149801 have disclosed some M1 PAM compounds. While several M1 PAMs have been disclosed in the literature till date, no drug acting as M1 PAM is launched in the market.

Although the prior arts disclose M1 PAM compounds that are useful in the treatment of CNS related diseases, there exist an issue of poor brain penetration and cholinergic side effects like hypersalivation, diarrhea and emesis. Therefore, there is an unmet need and scope to discover and develop new M1 PAMs with good brain penetration and with no cholinergic side effects for the treatment of CNS related disorders.

SUMMARY OF THE INVENTION

In first aspect, the present invention relates to M1 PAMs of compound of formula (I),

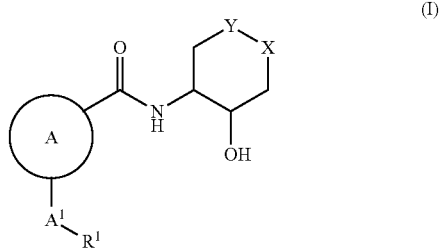

or an isotopic form, a stereoisomer, a tautomer or a pharmaceutically acceptable salt thereof; wherein:
$R^1$ is —$(C_{6-10})$-aryl or —$(C_{5-10})$-heteroaryl; each of which is optionally substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo $(C_{1-6})$-alkyl, —NH$_2$, —CN and $R^{1a}$;
$R^{1a}$ is —$(C_{6-10})$-aryl or —$(C_{5-10})$-heteroaryl; each of which is optionally substituted with one or more substituents selected from the group consisting of halogen, —OH, —NH$_2$, —CN, —O—$(C_{1-6})$-alkyl, —S—$(C_{1-6})$-alkyl, —$(C_{1-6})$-alkyl and —$(C_{3-6})$-cycloalkyl;
$A^1$ is CH$_2$ or CHF;
ring A is selected from the group consisting of:

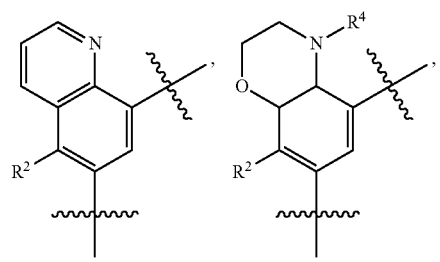

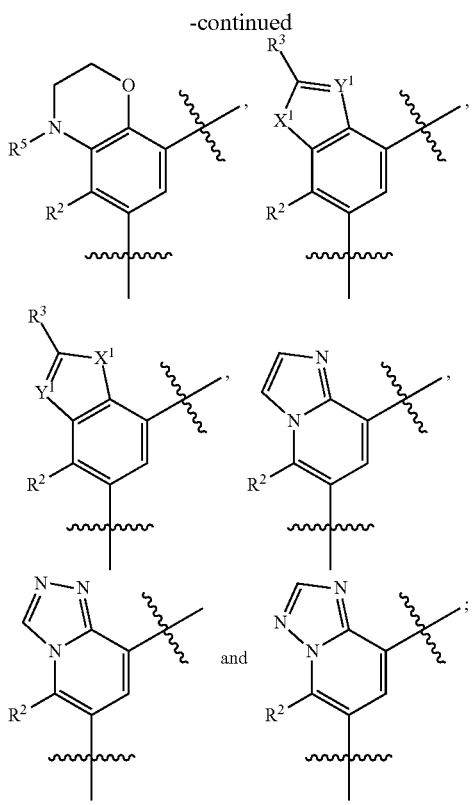

"⁓" represents point of attachment;
R² is hydrogen, —(C₁₋₆)-alkyl or —(C₃₋₆)-cycloalkyl;
R³ is hydrogen, halogen, —OH, —(C₁₋₆)-alkyl, —O—(C₁₋₆)-alkyl or halo(C₁₋₆)-alkyl;
R⁴ is hydrogen, —(C₁₋₆)-alkyl or halo(C₁₋₆)-alkyl;
R⁵ is hydrogen, —(C₁₋₆)-alkyl or halo(C₁₋₆)-alkyl;
X¹ is independently selected from O, S, NH or NCH₃;
Y¹ is independently selected from N or CH;
X is independently selected from CH₂, O, NH or NCH₃; and
Y is independently selected from CH₂, O, NH or NCH₃.

In another aspect, the present invention relates to the processes for preparing the compound of formula (I), or a stereoisomer or a pharmaceutically acceptable salt thereof.

In yet another aspect, the present invention relates to pharmaceutical composition containing a therapeutically effective amount of at least one compound of formula (I), or a stereoisomer or a pharmaceutically acceptable salt thereof and pharmaceutically acceptable excipients or carriers.

In yet another aspect, the present invention relates to compound of formula (I), or a stereoisomer or a pharmaceutically acceptable salt thereof in combination with one or more other therapeutic agents selected from acetylcholinesterase inhibitors and NMDA receptor antagonist.

In yet another aspect, the present invention relates to compound of formula (I), or a stereoisomer or a pharmaceutically acceptable salt thereof, for use as muscarinic M1 receptor positive allosteric modulators.

In yet another aspect, the present invention relates to compound of formula (I), or a stereoisomer or a pharmaceutically acceptable salt thereof, for use in the treatment of disease or disorders selected from cognitive, pain or sleep disorders.

In yet another aspect, the present invention relates to compound of formula (I), or a stereoisomer or a pharmaceutically acceptable salt thereof, for use in the treatment of disease or disorders selected from Alzheimer's disease, schizophrenia, Parkinson's disease dementia, dementia due to Lewy body, pain or sleep disorders.

In another aspect, the present invention relates to a method for the treatment of disease or disorders related to muscarinic M1 receptor, comprising administering to a patient in need thereof, a therapeutically effective amount of a compound of formula (I), or a stereoisomer or a pharmaceutically acceptable salt thereof.

In yet another aspect, the present invention relates to use of the compound of formula (I), or a stereoisomer or a pharmaceutically acceptable salt thereof, for the manufacture of a medicament for the treatment of disease or disorders related to muscarinic M1 receptors.

In yet another aspect, the present invention relates to compound of formula (I) or a stereoisomer or a pharmaceutically acceptable salt thereof, for use in positive allosteric modulation of muscarinic M1 receptor.

BRIEF DESCRIPTION OF DRAWINGS

FIG. 1: Effect of test compound (Example 11) in combination with donepezil on hippocampal theta oscillations.

DETAILED DESCRIPTION OF THE INVENTION

Unless otherwise stated, the following terms used in the specification and claims have the meanings given below:

The term, "(C₁₋₆)-alkyl" as used herein refers to branched or straight chain aliphatic hydrocarbon containing 1 to 6 carbon atoms. Examples of (C₁₋₆)-alkyl include methyl, ethyl, n-propyl, isopropyl, n-butyl, isobutyl, sec-butyl and tert-butyl. Preferably (C₁₋₆)-alkyl is methyl, ethyl or isopropyl.

The term, "halogen" or "halo" as used herein refers to fluorine, chlorine, bromine or iodine. Preferably, halogen is fluorine, chlorine or bromine. More preferably halogen is fluorine or chlorine.

The term "halo(C₁₋₆)-alkyl" as used herein refers to (C₁₋₆)-alkyl as defined above wherein one or more hydrogen of the same or different carbon atom is substituted with same or different halogens. Examples of halo(C₁₋₆)-alkyl include fluoromethyl, chloromethyl, fluoroethyl, difluoromethyl, dichloromethyl, trifluoromethyl, difluoroethyl and the like.

The term, "(C₃₋₆)-cycloalkyl" as used herein refers to saturated monocyclic hydrocarbon ring containing from three to six carbon atoms. Examples of (C₃₋₆)-cycloalkyl group include cyclopropyl, cyclobutyl, cyclopentyl and cyclohexyl.

The term, "(C₆₋₁₀)-aryl" as used herein refers to aromatic hydrocarbon rings containing six to ten carbon atoms. Examples of (C₆₋₁₀)-aryl group include phenyl or naphthyl.

The term, "(C₅₋₁₀)-heteroaryl" as used herein refers to aromatic monocyclic or aromatic bicyclic heterocycle ring systems containing five to ten atoms. Examples of (C₅₋₁₀)-heteroaryl group include 1,2,4-oxadiazolyl, 1,3,4-oxadiazolyl, 1,2,4-thiadiazolyl, 1,3,4-thiadiazolyl, triazolyl, tetrazolyl, triazinyl, furyl, imidazolyl, isoxazolyl, isothiazolyl, oxazolyl, pyrrolyl, pyrazolyl, thiazolyl, thienyl, pyridyl, pyrazinyl, pyrimidinyl, pyridazinyl, benzodioxolyl, benzofuranyl, benzofurazanyl, benzimidazolyl, benzopyrazolyl, benzothiazolyl, benzotriazolyl, benzothiophenyl, benzoxazepinyl, benzoxazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, isoquinolyl, quinolyl, phthalazinyl, naphthyridinyl, quinoxalinyl, quinazolinyl, and N-oxides thereof.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include $^2H$ (deuterium) and $^3H$ (tritium).

The term, "stereoisomers" as used herein refers to isomers of compound of formula (I) that differ in the arrangement of their atoms in space. Compounds disclosed herein may exist as single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Preferably the cognitive disorder is dementia. Example of dementia includes but not limited to, dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

The term, "patient" as used herein refers to an animal. Preferably the term "patient" refers to mammal. The term mammal includes animals such as mice, rats, dogs, rabbits, pigs, monkeys, horses, pigeons, *Xenopus laevis*, zebrafish, guinea pigs and humans. More preferably the patient is human.

EMBODIMENTS

The present invention encompasses all the compounds described by the compound of formula (I) without any limitation, however, preferred aspects and elements of the invention are discussed herein in the form of the following embodiments.

In one embodiment, the present invention relates to the compound of formula (I), wherein: ring A is selected from groups consisting of:

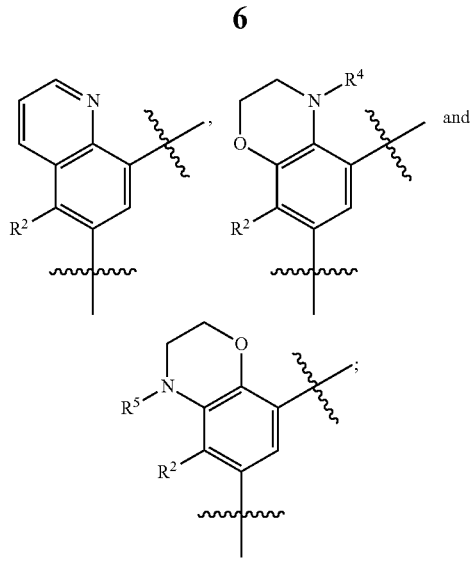

wherein $R^2$, $R^4$, $R^5$ and "〰" are as defined in first aspect; or an isotopic form, a stereoisomer or a pharmaceutically acceptable salt thereof.

In another embodiment, the present invention relates to the compound of formula (I), wherein ring A is selected from groups consisting of:

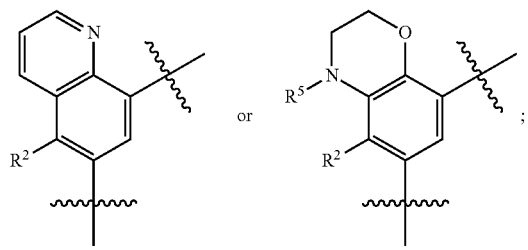

wherein $R^2$, $R^5$ and "〰" are as defined in first aspect; or an isotopic form, a stereoisomer or a pharmaceutically acceptable salt thereof.

In another embodiment, the present invention relates to the compound of formula (I), wherein ring A is selected from groups consisting of:

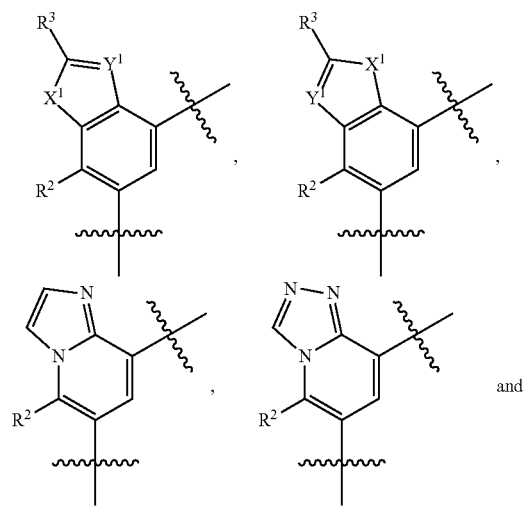

-continued

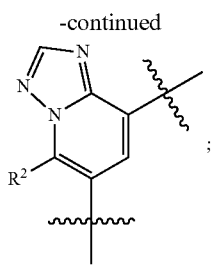

wherein $X^1$, $Y^1$, $R^2$ and $R^3$ are as defined in first aspect; or an isotopic form, a stereoisomer or a pharmaceutically acceptable salt thereof.

In another embodiment, the present invention relates to the compound of formula (I), wherein ring A is selected from groups consisting of:

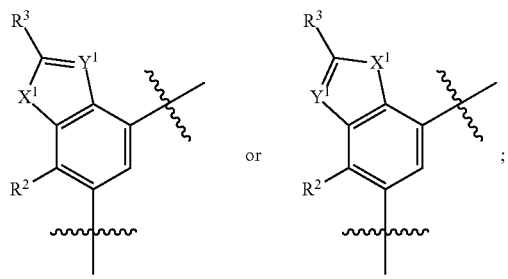

wherein $X^1$, $Y^1$, $R^2$, $R^3$ and "⁓" are as defined in first aspect; or an isotopic form, a stereoisomer or a pharmaceutically acceptable salt thereof.

In another embodiment, the present invention relates to the compound of formula (I), wherein: ring A is selected from groups consisting of:

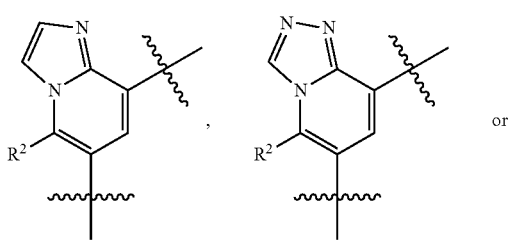

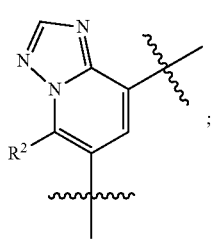

wherein $R^2$ and "⁓" are as defined in first aspect; or an isotopic form, a stereoisomer or a pharmaceutically acceptable salt thereof.

In another embodiment, the present invention relates to the compound of formula (I), wherein: ring A is

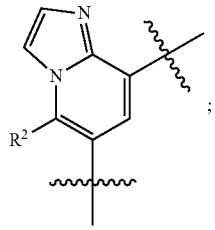

wherein $R^2$ and "⁓" are as defined in first aspect; or an isotopic form, a stereoisomer or a pharmaceutically acceptable salt thereof.

wherein: $R^1$ is —$(C_{6-10})$-aryl or —$(C_{5-10})$-heteroaryl; each of which is optionally substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$ and —CN or an isotopic form, a stereoisomer or a pharmaceutically acceptable salt thereof.

In another embodiment, the present invention relates to the compound of formula (I), wherein: $R^1$ is —$(C_{6-10})$-aryl or —$(C_{5-10})$-heteroaryl; each of which is substituted with one or more substituents selected from $R^{1a}$, halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$ and —CN; wherein $R^{1a}$ is as defined in the first aspect; or an isotopic form, a stereoisomer or a pharmaceutically acceptable salt thereof.

In another embodiment, the present invention relates to the compound of formula (I), wherein: $R^1$ is —$(C_{6-10})$-aryl optionally substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$ and —CN or an isotopic form, a stereoisomer or a pharmaceutically acceptable salt thereof.

In another embodiment, the present invention relates to the compound of formula (I), wherein: $R^1$ is —$(C_{5-10})$-heteroaryl optionally substituted with one or more substituents selected from halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$ and —CN or an isotopic form, a stereoisomer or a pharmaceutically acceptable salt thereof.

In another embodiment, the present invention relates to the compound of formula (I), wherein: $R^1$ is —$(C_{6-10})$-aryl substituted with one or more substituents selected $R^{1a}$, halogen, —OH, —O—$(C_{1-6})$-alkyl, —S—$(C_{1-6})$-alkyl, —N(CH$_3$)$_2$, —$(C_{1-6})$-alkyl, —$(C_{3-6})$-cycloalkyl, halo$(C_{1-6})$-alkyl, —NH$_2$, —CONH$_2$ and —CN; wherein $R^{1a}$ is as defined in the first aspect; or an isotopic form, a stereoisomer or a pharmaceutically acceptable salt thereof.

In another embodiment, the present invention relates to the compound of formula (I), wherein: $R^1$ is —$(C_{5-10})$-heteroaryl substituted with one or more $R^{1a}$; wherein $R^{1a}$ is as defined in the first aspect; or an isotopic form, a stereoisomer or a pharmaceutically acceptable salt thereof.

In another embodiment, the preferred compound of the invention is selected from the group consisting of:
N-(cis-1S,2S-2-Hydroxycyclohexyl)-6-(2-chloropyridin-4-ylmethyl)-5-methylquinoline-8-carboxamide;
N-(cis-1S,2S-2-Hydroxycyclohexyl)-6-(2,3-difluorobenzyl)-5-methylquinoline-8-carboxamide;

N-(cis-3S,4S-3-Hydroxytetrahydropyran-4-yl)-6-(2-chloropyridin-5-ylmethyl)-5-methylquinoline-8-carboxamide;

N-(cis-1S,2S-2-Hydroxycyclohexyl)-6-(2-fluoropyridin-4-ylmethyl)-5-methylquinoline-8-carboxamide;

N-(cis-1S,2S-2-Hydroxycyclohexyl)-6-(2-fluorobenzyl)-5-methylquinoline-8-carboxamide;

N-(cis-1S,2S-2-Hydroxycyclohexyl)-6-(2-chloropyridin-5-ylmethyl)-5-methylquinoline-8-carboxamide;

N-(cis-1S,2S-2-Hydroxycyclohexyl)-6-[2-(1-methyl-1H-pyrazol-4-yl)-pyridin-5-ylmethyl]-5-methylquinoline-8-carboxamide;

N-(cis-1S,2S-2-Hydroxycyclohexyl)-6-[2,3-difluoro-4-(1-methyl-1H-pyrazol-4-yl)-benzyl]-5-methylquinoline-8-carboxamide;

N-(cis-1S,2S-2-Hydroxycyclohexyl)-6-[3-fluoro-4-(1-methyl-1H-pyrazol-4-yl)-benzyl]-5-methylquinoline-8-carboxamide;

N-(cis-1S,2S-2-Hydroxycyclohexyl)-6-(4-pyrazol-1-yl-benzyl)-5-methylquinoline-8-carboxamide;

N-(cis-1S,2S-2-Hydroxycyclohexyl)-6-[2-fluoro-4-(1-methyl-1H-pyrazol-4-yl)-benzyl]-5-methylquinoline-8-carboxamide;

N-(cis-1S,2S-2-Hydroxycyclohexyl)-6-(4-thiazol-4-yl-benzyl)-5-methylquinoline-8-carboxamide;

N-(cis-3S,4S-3-Hydroxytetrahydropyran-4-yl)-6-(4-thiazol-4-yl-benzyl)-5-methylquinoline-8-carboxamide;

N-(cis-1S,2S-2-Hydroxycyclohexyl)-6-benzyl-5-methylquinoline-8-carboxamide;

N-(cis-1S,2S-2-Hydroxycyclohexyl)-6-[4-(1-methyl-1H-pyrazol-4-yl)-benzyl]-5-methylquinoline-8-carboxamide;

N-(cis-1S,2S-2-Hydroxycyclohexyl)-6-[4-(1-methyl-1H-pyrazol-4-yl)-benzyl]-5-methyl-3,4-dihydro-2H-benzo[1,4]oxazine-8-carboxamide;

N-(cis-1S,2S-2-Hydroxycyclohexyl)-6-(4-pyrazol-1-yl-benzyl)-5-methyl-3,4-dihydro-2H-benzo[1,4]oxazine-8-carboxamide;

N-(cis-1S,2S-2-Hydroxycyclohexyl)-5-methyl-6-[4-(1-methyl-1H-pyrazol-4-yl)-benzyl]-imidazo[1,2-a]pyridine-8-carboxamide;

N-(cis-1S,2S-2-Hydroxycyclohexyl)-5-methyl-6-(4-pyrazol-1-yl-benzyl)-imidazo[1,2-a]pyridine-8-carboxamide;

N-(cis-1S,2S-2-Hydroxycyclohexyl)-5-methyl-6-[2-fluoro-4-(1-methyl-1H-pyrazol-4-yl)-benzyl]-imidazo[1,2-a]pyridine-8-carboxamide;

N-(cis-1S,2S-2-Hydroxycyclohexyl)-6-[2,3-difluoro-4-(1-methyl-1H-pyrazol-4-yl)-benzyl]-imidazo[1,2-a]pyridine-8-carboxamide;

N-(cis-1S,2S-2-Hydroxycyclohexyl)-6-(2.3-difluorobenzyl)-imidazo[1,2-a]pyridine-8-carboxamide;

N-(cis-1S,2S-2-Hydroxycyclohexyl)-6-(4-thiazol-4-yl-benzyl)-imidazo[1,2-a]pyridine-8-carboxamide;

N-(cis-1S,2S-2-Hydroxycyclohexyl)-6-(4-phenyl-benzyl)-imidazo[1,2-a]pyridine-8-carboxamide;

N-(cis-1S,2S-2-Hydroxycyclohexyl)-6-[4-(1-methyl-1H-pyrazol-4-yl)-benzyl]-imidazo[1,2-a]pyridine-8-carboxamide;

N-(cis-1S,2S-2-Hydroxycyclohexyl)-6-[2-fluoro-4-(1-methyl-1H-pyrazol-4-yl)-benzyl]-imidazo[1,2-a]pyridine-8-carboxamide;

N-(cis-1S,2S-2-Hydroxycyclohexyl)-7-methyl-6-(4-pyrazol-1-yl-benzyl)-1H-benzimidazole-4-carboxamide;

N-(cis-1S,2S-2-Hydroxycyclohexyl)-7-methyl-6-[4-(1-methyl-1H-pyrazol-4-yl)-benzyl]-1H-benzimidazole-4-carboxamide;

N-(cis-1S,2S-2-Hydroxycyclohexyl)-6-[4-(1-methyl-1H-pyrazol-4-yl)-benzyl]-1H-benzimidazole-4-carboxamide;

N-(cis-1S,2S-2-Hydroxycyclohexyl)-7-methyl-6-[2-fluoro-4-(1-methyl-1H-pyrazol-4-yl)-benzyl]-1H-benzimidazole-4-carboxamide;

N-(cis-1S,2S-2-Hydroxycyclohexyl)-7-methyl-6-[2-chloropyridin-3-ylmethyl]-1H-benzimidazole-4-carboxamide;

N-(cis-1S,2S-2-Hydroxycyclohexyl)-7-methyl-6-[4-(thiazol-4-yl)-benzyl]-1H-benzimidazole-4-carboxamide;

N-(cis-1S,2S-2-Hydroxycyclohexyl)-7-methyl-6-[2,3-difluorobenzyl]-1H-benzimidazole-4-carboxamide;

N-(cis-1S,2S-2-Hydroxycyclohexyl)-7-methyl-6-[3,4-difluorobenzyl]-1H-benzimidazole-4-carboxamide;

N-(cis-1S,2S-2-Hydroxycyclohexyl)-7-methyl-6-[6-(1-methyl-1H-pyrazol-4-yl)-pyridin-3-ylmethyl]-1H-benzimidazole-4-carboxamide;

N-(cis-1S,2S-2-Hydroxycyclohexyl)-7-methyl-6-[2,3-difluoro-4-(1-methyl-1H-pyrazol-4-yl)-benzyl]-1H-benzimidazole-4-carboxamide;

N-(cis-1S,2S-2-Hydroxycyclohexyl)-6-[2,3-difluoro-4-(1-methyl-1H-pyrazol-4-yl)-benzyl]-1H-benzimidazole-4-carboxamide;

N-(cis-1S,2S-2-Hydroxycyclohexyl)-2,7-dimethyl-6-(4-pyrazol-1-yl-benzyl)-1H-benzimidazole-4-carboxamide;

N-(cis-1S,2S-2-Hydroxycyclohexyl)-2,7-dimethyl-6-[4-(1-methyl-1H-pyrazol-4-yl)-benzyl]-1H-benzimidazole-4-carboxamide;

N-(cis-1S,2S-2-Hydroxycyclohexyl)-2,7-dimethyl-6-(4-thiazol-4-yl-benzyl)-1H-benzimidazole-4-carboxamide;

N-(cis-1S,2S-2-Hydroxycyclohexyl)-3,7-dimethyl-6-[2-fluoro-4-(1-methyl-1H-pyrazol-4-yl)-benzyl]-3H-benzimidazole-4-carboxamide;

N-(cis-1S,2S-2-Hydroxycyclohexyl)-3,7-dimethyl-6-[4-(1-methyl-1H-pyrazol-4-yl)-benzyl]-3H-benzimidazole-4-carboxamide;

N-(cis-1S,2S-2-Hydroxycyclohexyl)-3,7-dimethyl-6-[2,3-difluoro-4-(1-methyl-1H-pyrazol-4-yl)-benzyl]-3H-benzimidazole-4-carboxamide;

N-(cis-1S,2S-2-Hydroxycyclohexyl)-3,7-dimethyl-6-[6-(1-methyl-1H-pyrazol-4-yl)-pyridin-3-ylmethyl]-3H-benzimidazole-4-carboxamide;

N-(cis-1S,2S-2-Hydroxycyclohexyl)-3,7-dimethyl-6-[4-(thiazol-4-yl)-benzyl]-3H-benzimidazole-4-carboxamide; and N-(cis-1S,2S-2-Hydroxycyclohexyl)-2,4-dimethyl-5-[4-(1-methyl-1H-pyrazol-4-yl)-benzyl]-benzofuran-7-carboxamide;

or a pharmaceutically acceptable salt thereof.

Experimental Procedures

Scheme-1 depicts general processes for preparation of the compound of formula (I), wherein: T is —($C_{1-6}$)-alkyl, $A^1$ is $CH_2$; ring A, $R^1$, X and Y are as defined above.

Scheme-1

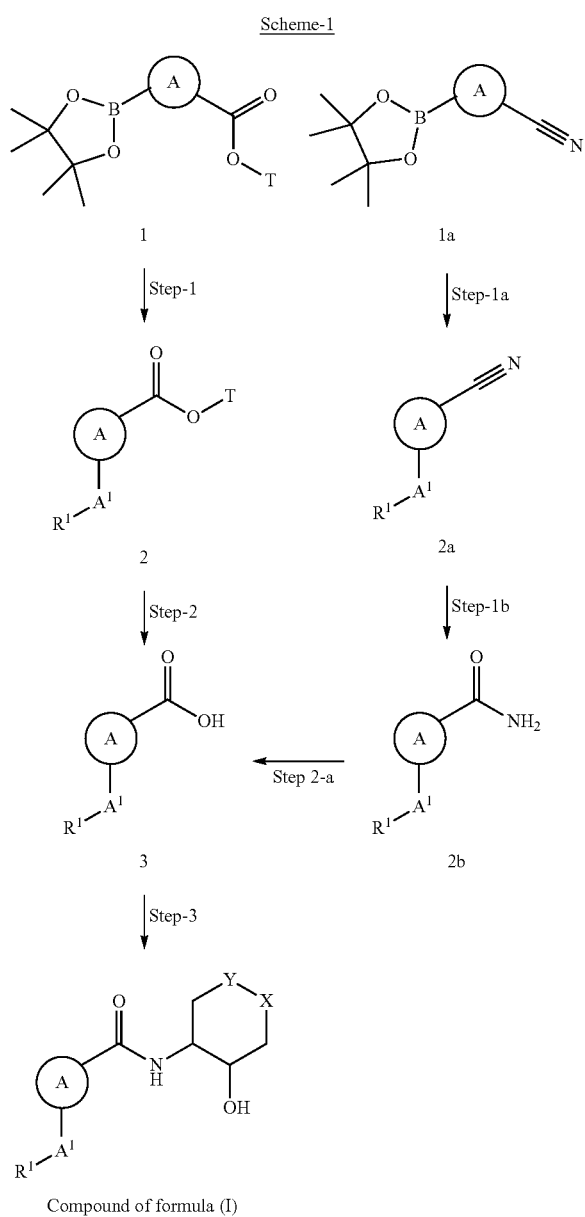

Compound of formula (I)

Step-1: Preparation of Compound of Formula 2

The compound of formula 1 is reacted with the compound of formula A,

R¹-A¹-Cl    A in presence of [1,1'-bis(diphenylphosphino)ferrocene]palladium(II) dichloride and a base selected from potassium carbonate, cesium carbonate and sodium carbonate in a mixture of solvents such as water, THF and 1,4-dioxane under reflux for 3 to 7 h to obtain the compound of formula 2.

Step-2: Preparation of Compound of Formula 3

The compound of formula 2 is hydrolyzed to compound of formula 3 in a mixture of solvents such as water, THF and methanol using sodium hydroxide under reflux for 2 to 17 h.

Step-1a: Preparation of Compound of Formula 2a

The compound of formula 1a is reacted with the compound of formula A,

R¹-A¹-Cl    A in presence of [1,1'-bis(diphenylphosphino)ferrocene]palladium(II) dichloride and a base selected from potassium carbonate and sodium carbonate in a mixture of solvents such as water and 1,4-dioxane under reflux for 3 to 5 h to obtain the compound of formula 2a.

Step-1b: Preparation of Compound of Formula 2b

The compound of formula 2a is hydrolyzed to compound of formula 2b in a mixture of solvents such as water and ethanol using potassium hydroxide under reflux for 2 to 4 h.

Step-2a: Preparation of Compound of Formula 3

The compound of formula 2b is hydrolyzed to compound of formula 3 using aq. HCl at a temperature in the range of 95° C. to 105° C. for 5 to 7 h.

Step-3: Preparation of Compound of Formula (I)

The compound of formula 3 is coupled with amine,

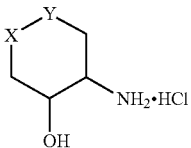

in presence of coupling reagent, HATU, DCC, or EDC and a base, DIPEA in a solvent selected from DMF, THF, dichloromethane or 1,4-dioxane at RT overnight to obtain the compound of formula (I).

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric or phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

Preparation of Stereoisomers of Compound of Formula (I)

The stereoisomers of compounds of formula (I) may be prepared by one or more conventional ways presented below:
a. One or more of the reagents may be used in their optically active form.
b. Optically pure catalyst or chiral ligands along with metal catalyst may be employed in the reduction process. The metal catalyst may be rhodium, ruthenium, indium and the like. The chiral ligands may preferably be chiral phosphines.
c. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography and the like, which is followed by an additional step of isolating the optically active product from the resolved material/salt.

d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

In another embodiment, the suitable pharmaceutically acceptable salt includes hydrochloride, hydrobromide, oxalate, fumarate, tartrate, maleate and succinate.

In another aspect of the present invention, the compound of formula (I) are muscarinic M1 positive allosteric modulators.

In another aspect, the present invention relates to a method of treating the disease or disorder selected from cognitive disorder, schizophrenia, pain or sleep disorders, comprising administering to a patient in need thereof, a therapeutically effective amount of compounds of formula (I) or a pharmaceutically acceptable salt thereof.

In another aspect, the present invention relates to a method of treatment of Alzheimer's diseases comprising administering to a patient in need thereof, a therapeutically effective amount of compounds of formula (I) or a pharmaceutically acceptable salt thereof.

In another aspect, the present invention relates to a method of treatment of Alzheimer's diseases including mild Alzheimer's disease, moderate Alzheimer's disease, severe Alzheimer's disease, mild to moderate Alzheimer's disease or moderate to severe Alzheimer's disease, comprising administering to a patient in need thereof, a therapeutically effective amount of compounds of formula (I) or a pharmaceutically acceptable salt thereof.

In yet another aspect, the present invention relates to compound of formula (I) for use in the treatment of disease or disorder selected from cognitive disorder, schizophrenia, pain or sleep disorders.

In yet another aspect, the present invention relates to use of the compound of formula (I) in the manufacture of medicament for the treatment of diseases or disorder selected from cognitive disorder, schizophrenia, pain or sleep disorders.

In yet another aspect, the present invention relates to use of the compound of formula (I) in the manufacture of medicament for the treatment of diseases or disorder selected from cognitive disorder.

In yet another aspect, the present invention relates to use of the compound of formula (I) in the manufacture of medicament for the treatment of Alzheimer's disease.

In yet another embodiment, the present invention relates to the combination of compound of formula (I) with one or more other therapeutic agents such as acetylcholinesterase inhibitors and NMDA receptor antagonist.

In another embodiment, the compound of formula (I) of the present invention may be used in combination with one or more other therapeutic agents in the treatment of diseases or disorders for which the compound of formula (I) of the present invention have utility.

Examples of the combinations of the compounds of present invention include combination with the therapeutic agents for the treatment of Alzheimer's disease, for example acetylcholinesterase inhibitors such as galantamine, rivastigmine, donepezil, and tacrine; and NMDA receptor antagonist such as memantine.

In yet another embodiment, the present invention relates to combination of compound of formula (I) with at least one therapeutic agents selected from galantamine, rivastigmine, donepezil, tacrine and memantine.

In yet another embodiment the present invention relates to the combination of compound of formula (I) with one or more other therapeutic agents such as acetylcholinesterase inhibitors and NMDA receptor antagonist for use in the treatment of cognitive disorder, schizophrenia, pain and sleep disorders.

In yet another embodiment the present invention relates to the combination of compound of formula (I) with one or more other therapeutic agents acetylcholinesterase inhibitors and NMDA receptor antagonist for use in the treatment of Alzheimer's disease.

In yet another aspect, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

The dose of the active compounds can vary depending on factors such as age and weight of patient, nature and severity of the disease to be treated and such other factors.

Therefore, any reference regarding pharmacologically effective amount of the compounds of general formula (I), stereoisomers and pharmaceutically acceptable salts thereof refers to the aforementioned factors.

The following abbreviations are used herein:
AMP: Adenosine monophosphate
AUC: Area under the curve
$C_{max}$: Maximum concentration
$CDCl_3$: Deuterated chloroform
$Cs_2CO_3$: Caesium carbonate
DCM: Dichloromethane
DCC: N,N'-Dicyclohexylcarbodiimide
DIPEA: N,N-Diisopropylethylamine
DMF: N,N-Dimethylformamide
DMSO: Dimethyl sulfoxide
$EC_{50}$: Half maximal effective concentration
EDC: Ethylene dichloride
EtOAc: Ethyl acetate
EtOH: Ethanol
h: Hour (s)
HATU: 2-(7-Aza-1H-benzotriazole-1-yl)-1,1,3,3-tetramethyluronium hexafluorophosphate
HCl: Hydrochloric acid
$H_2O$: Water
$H_2SO_4$: Sulphuric acid
$K_2CO_3$: Potassium carbonate
$KNO_3$: Potassium nitrate
LC-MS/MS: Liquid chromatography-Mass spectrometry/Mass spectrometry
mmol: millimole(s)
$NaHCO_3$: Sodium bicarbonate
NaOH: Sodium hydroxide
$Na_2SO_4$: Sodium sulphate
$NH_4Cl$: Ammonium chloride
RT: Room temperature (25° C. to 30° C.)
ROA: Route of Administration
p.o: Per Oral
THF: Tetrahydrofuran
$T_{1/2}$: Half-life time
X-Phos: 2-Dicyclohexylphosphino-2',4',6'-triisopropylbiphenyl

EXAMPLES

The compounds of the present invention were prepared according to the following experimental procedures, using appropriate materials and conditions. The following examples are provided by way of illustration only but not to limit the scope of present invention.

Preparation of Intermediates

Intermediate 1:
6-Bromo-5-methylquinoline-8-carboxylic acid (I-1)

To a stirred solution of 2-amino-5-bromo-4-methyl-benzoic acid (15.9 g, 69.1 mmol) in nitrobenzene (22.8 mL) at RT, glycerol (24.8 g, 269.6 mmol) followed by con. $H_2SO_4$ (22.28 g, 222.8 mmol) were added. Reaction mixture was gradually heated to 125° C. and was stirred at this temperature for 16 h. After cooling it to RT, the reaction mixture was quenched with ice & diluted with water and EtOAc. The two layers were separated and aqueous layer was extracted with EtOAc. The aqueous layer was further extracted with 10% ammonical methanol DCM solvent system. The combined organic layer was washed once with brine solution, dried over anhydrous $Na_2SO_4$ and the solvent was removed under reduced pressure to obtain the title compound.

Yield: 9.65 g (52%); $^1$H-NMR (400 MHz, $CDCl_3$): δ 16.49 (bs, 1H), 8.94 (s, 1H), 8.93 (d, J=6.2 Hz, 1H), 7.69 (dd, J=4.3, 8.6 Hz, 1H), 2.87 (s, 3H); Mass (m/z): 265.8, 267.8 (M+H)$^+$.

Intermediate 2: Methyl 6-bromo-5-methylquinoline-8-carboxylate (I-2)

To a stirred solution of 6-bromo-5-methyl-quinoline-8-carboxylic acid (I-1), (9.65 g, 36.2 mmol) in methanol (145.1 mL) cooled at 0° C., thionyl chloride (15.7 mL, 145.1 mmol) was slowly added. Reaction mixture was gradually heated to reflux temperature and was stirred at this temperature for 16 h. After cooling it to RT, the volatiles were removed under reduced pressure and the crude product was dissolved in 10% aqueous $NaHCO_3$ and EtOAc. The two layers were separated and aqueous layer was extracted with EtOAc. The combined organic layer was washed once with brine solution, dried over anhydrous $Na_2SO_4$ and the solvent was removed under reduced pressure to obtain a crude product which was purified by silica gel column chromatography to obtain the title compound.

Yield: 9.7 g; $^1$H-NMR (400 MHz, $CDCl_3$): δ 9.05 (d, J=3.8 Hz, 1H), 8.42 (d, J=8.5 Hz, 1H), 8.18 (s, 1H), 7.52 (dd, J=4.0 Hz, 8.5 Hz 1H), 4.04 (s, 3H), 2.81 (s, 3H); Mass (m/z): 280.1, 282.1 (M+H)$^+$.

Intermediate 3: tert-Butyl (3-cyano-6-methylpyridin-2-yl)-carbamate (I-3)

To a stirred solution of 2-chloro-6-methyl-nicotinonitrile (0.4 g, 2.62 mmol) in dry THF (10.4 mL) cooled at 0° C., sequential addition of tert-butylcarbamate (1.5 g, 13.1 mmol) $Cs_2CO_3$ (3.25 g, 9.99 mmol), X-Phos (0.025 g, 0.052 mmol) and tris(dibenzilidineacetone)dipalladium[0] (0.12 g, 0.13 mmol) was done. Reaction mixture was gradually heated to 65° C. and was stirred at this temperature for 7 h. After cooling it to RT, additional amount of $Cs_2CO_3$ (3.25 g, 9.99 mmol) was added. Reaction mixture was gradually heated to 65° C. and was stirred at this temperature for another 7 h. The reaction mixture was cooled to RT, and was filtered through celite bed. The celite bed was washed with EtOAc. The filtrate was washed with 10% aqueous $NaHCO_3$ solution. The organic layer was washed once with brine solution, dried over anhydrous $Na_2SO_4$ and the solvent was removed under reduced pressure to obtain the title compound.

Yield: 0.55 g (87%); $^1$H-NMR (400 MHz, $CDCl_3$): δ 7.82 (d, J=5.6 Hz, 1H), 7.29 (bs, 1H), 7.00 (d, J=7.80 Hz, 1H), 2.56 (s, 1H), 1.47 (s, 9H); Mass (m/z): 234.1 (M+H)$^+$.

Intermediate 4: 2-Amino-6-methylnicotinonitrile (I-4)

To a stirred solution of tert-Butyl (3-cyano-6-methyl-pyridin-2-yl)-carbamate (I-3), (0.55 g, 2.36 mmol) in DCM (9.4 mL) cooled at 0° C., TFA (0.22 mL, 10.7 mmol) was added. The reaction mixture was gradually warmed to RT, and was stirred at this temperature for 16 h. The volatiles were removed under reduced pressure and crude mass was diluted with 10% aqueous $NaHCO_3$ solution and EtOAc. The two layers were separated. The organic layer was washed with brine solution, dried over anhydrous Na$_2$SO$_4$ and the solvent was removed under reduced pressure to obtain the title compound.

Yield: 0.31 g (100%); $^1$H-NMR (400 MHz, DMSO): δ 7.73 (d, J=7.60 Hz, 1H), 6.78 (bs, 2H), 6.53 (d, J=8 Hz, 1H), 2.34 (s, 3H); Mass (m/z): 134.0 (M+H)$^+$.

Intermediate 5:
2-Amino-5-bromo-6-methylnicotinonitrile (I-5)

To a stirred solution of 2-amino-6-methyl-nicotinonitrile (I-4), (0.31 g, 2.3 mmol) in 1, 2-dichloroethane (9.4 mL) at RT, freshly recrystallized NBS (0.46 g, 2.6 mmol) was added. Reaction mixture was gradually heated to 85° C. and was stirred at this temperature for 3 h. The reaction mixture was cooled to RT, and was diluted with water and CHCl$_3$. The two layers were separated. The organic layer was washed with brine solution, dried over anhydrous Na$_2$SO$_4$ and the solvent was removed under reduced pressure to obtain the title compound.

Yield: 0.38 g (87%); $^1$H-NMR (400 MHz, CDCl$_3$): δ 7.74 (s, 1H), 5.12 (bs, 2H), 2.52 (s, 3H); Mass (m/z): 212.0, 214.0 (M+H)$^+$.

Intermediate 6: 6-Bromo-5-methylimidazo[1,2-a]pyridine-8-carbonitrile (I-6)

To a stirred solution of 2-amino-5-bromo-6-methyl-nicotinonitrile (I-5), (0.38 g, 1.8 mmol) in ethanol (7.1 mL) at RT, chloroacetaldehyde (49% aqueous solution, 0.23 mL, 3.56 mmol) was added. Reaction mixture was gradually heated to 85° C. and was stirred at this temperature for 6 h. The reaction mixture was cooled to RT, the volatiles were removed under reduced pressure and the crude product was purified by silica gel column chromatography to obtain the title compound.

Yield: 0.1 g (23%); $^1$H-NMR (400 MHz, CDCl$_3$): δ 7.87 (s, 1H), 7.83 (s, 1H), 7.66 (s, 1H), 2.86 (s, 3H); Mass (m/z): 235.9, 238.0 (M+H)$^+$.

Intermediate 7: Methyl 2-acetylamino-5-bromo-4-methylbenzoate (I-7)

To a stirred solution of methyl 2-amino-5-bromo-4-methyl-benzoate (2.0 g, 8.19 mmol) in dry DCM (32.7 mL) cooled at 0° C., triethylamine (1.7 mL, 8.2 mmol) acetyl chloride (0.65 g, 8.19 mmol) were added in sequence. The reaction was gradually brought to RT, and stirred for 2 h before being diluted with DCM and water. The two layers were separated and the organic layer was washed with brine solution, dried over anhydrous Na$_2$SO$_4$ and the solvent was removed under reduced pressure to obtain the title compound.

Yield: 2.3 g (95%); $^1$H-NMR (400 MHz, DMSO): δ 10.46 (bs, 1H), 8.22 (s, 1H), 7.99 (s, 1H), 3.85 (s, 3H), 2.37 (s, 3H), 2.12 (s, 3H); Mass (m/z): 286.0, 288.2 (M+H)$^+$.

Intermediate 8: Methyl 2-acetylamino-5-bromo-4-methyl-3-nitrobenzoate (I-8)

The methyl 2-acetylamino-5-bromo-4-methyl-benzoate (I-7), (1.0 g, 3.49 mmol) was added to fuming nitric acid (98%, 3.5 mL) cooled at 0° C. over a period of 15 minutes. After stirring for another 15 minutes, the reaction mixture was quenched by adding ice-water and EtOAc. The two layers were separated and the aqueous layer was further extracted with EtOAc. The combined organic layer was washed once with brine solution, dried over anhydrous Na$_2$SO$_4$ and the solvent was removed under reduced pressure to obtain the title compound as brown solid (1.0 g) in 95% yield. $^1$H-NMR (400 MHz, DMSO): δ 10.49 (s, 1H), 8.17 (s, 1H), 3.79 (s, 3H), 2.34 (s, 3H), 1.97 (s, 3H); Mass (m/z): 330.9, 332.9 (M+H)$^+$.

Intermediate 9: Ethyl 6-bromo-2,7-dimethyl-1H-benzimidazole-4-carboxylate (I-9)

To a stirred solution of methyl 2-acetylamino-5-bromo-4-methyl-3-nitrobenzoate (I-8), (1.0 g, 3.02 mmol) in a 1:2:4 mixture of H$_2$O:THF:EtOH (12.0 mL) at RT, iron powder (0.85 g, 15.1 mmol) and NH$_4$Cl (0.82 g, 15.1 mmol) were added. The reaction was gradually heated to reflux and stirred for 2 h. After cooling the reaction mass to RT, it was filtered through celite bed. The celite bed was washed with ethanol. The filtrate was evaporated under reduced pressure and the crude mass thus obtained was diluted with EtOAc and water. The two layers were separated and the organic layer was washed with brine solution, dried over anhydrous Na$_2$SO$_4$ and the solvent was removed under reduced pressure to obtain the crude product which was purified by silica gel column chromatography to obtain above titled compound.

Yield: 0.47 g (50%); $^1$H-NMR (400 MHz, DMSO): δ 12.40 (s, 1H), 7.84 (s, 1H), 4.44 (q, 2H), 2.61 (s, 3H), 2.56 (s, 3H), 1.37 (t, J=7.0 Hz, 3H); Mass (m/z): 297.0, 299.0 (M+H)$^+$.

Intermediate 10: Methyl 2-formylamino-5-bromo-4-methylbenzoate (I-10)

To a stirred solution of methyl 2-amino-5-bromo-4-methylbenzoate (2.0 g, 8.19 mmol) in formic acid (32.7 mL) heated to 100° C., and was stirred at this temperature for 16 h. The reaction was gradually cooled to RT, and was diluted with EtOAc and water. The two layers were separated and the organic layer was washed with brine solution, dried over anhydrous Na$_2$SO$_4$ and the solvent was removed under reduced pressure to obtain the title compound.

Yield: 2.0 g (90%); $^1$H-NMR (400 MHz, CDCl$_3$): δ 10.91 (bs, 1H), 8.65 (s, 1H), 8.50 (s, 1H), 8.19 (s, 1H), 3.91 (s, 3H), 2.45 (s, 3H); Mass (m/z): 272.2, 274.0 (M+H)$^+$.

Intermediate 11: Methyl 2-formylamino-5-bromo-4-methyl-3-nitrobenzoate (I-11)

The methyl 2-formylamino-5-bromo-4-methyl-benzoate (I-10), (2.5 g, 9.19 mmol) was added to fuming nitric acid (98%, 9.2 mL) cooled at 0° C. over a period of 15 minutes. After stirring for another 15 minutes, the reaction mixture was quenched by adding ice-water and EtOAc. The two layers were separated and the aqueous layer was further extracted with EtOAc. The combined organic layer was washed once with brine solution, dried over anhydrous Na$_2$SO$_4$ and the solvent was removed under reduced pressure to obtain the title compound.

Yield: 2.0 g (70%); $^1$H-NMR (400 MHz, CDCl$_3$): δ 9.47 (bs, 1H), 8.33 (s, 1H), 8.31 (s, 1H), 3.98 (s, 3H), 2.50 (s, 3H); Mass (m/z): 315.2, 317.0 (M+H)$^+$.

Intermediate 12: Ethyl 6-bromo-7-methyl-1H-benzimidazole-4-carboxylate (I-12)

To a stirred solution of methyl 2-formylamino-5-bromo-4-methyl-3-nitrobenzoate (I-11), (2.0 g, 6.31 mmol) in a 1:2:4 mixture of H$_2$O:THF:EtOH (25.0 mL) at RT, iron powder (1.76 g, 31.55 mmol) and NH$_4$Cl (1.7 g, 31.55 mmol) were added. The reaction was gradually heated to reflux and stirred for 6 h. After cooling the reaction mass to RT, it was filtered through celite bed. The celite bed was washed with ethanol. The filtrate was evaporated under reduced pressure and the crude mass thus obtained was diluted with EtOAc and water. The two layers were separated and the organic layer was washed with brine solution, dried over anhydrous Na$_2$SO$_4$ and the solvent was removed under reduced pressure to obtain the crude product which was purified by silica gel column chromatography to obtain above titled compound.

Yield: 0.72 g (40%); $^1$H-NMR (400 MHz, CDCl$_3$): δ 10.51 (bs, 1H), 8.10 (s, 2H), 4.47 (q, 2H), 2.79 (s, 3H), 1.44 (t, J=6.8 Hz, 3H); Mass (m/z): 282.9, 285.0 (M+H)$^+$.

Intermediate 13: Methyl 2-hydroxy-4-methylbenzoate (I-13)

To a solution of 2-hydroxy-4-methyl-benzoic acid (10 g, 0.065 mol) in methanol (50 mL) was added thionylchloride (15 mL, mole) at 0° C. The reaction mixture was heated at 80° C. for 12 h, cooled to RT, concentrated under vacuum to obtain the crude. To the crude 200 mL of water was added and basified with aqueous ammonia, and extracted with dichloromethane (200 mL×3). Organic layer was washed with brine solution (50 mL) and dried over Na$_2$SO$_4$. Organic layer was concentrated under vacuum to afford the title compound.

Yield: 10.7 g (98.1%); $^1$H-NMR (CDCl$_3$, 400 MHz) δ ppm: 2.34 (s, 3H), 3.92 (s, 3H), 6.68-6.70 (d, J=8 Hz, 1H), 6.79 (s, 1H), 7.69-7.71 (d, J=8.12 Hz, 1H), 10.71 (s, 1H); Mass (m/z): 167.1 (M+H)$^+$.

Intermediate 14: Methyl 5-bromo-2-hydroxy-4-methylbenzoate (I-14)

To a solution of methyl 2-hydroxy-4-methyl-benzoate (10.6 g, 0.06 mol) in chloroform (20 mL) was added dropwise bromine (3.27 mL, 0.06 mol) at 0° C. and the mixture was stirred at room temperature for 3 h. The reaction mixture was concentrated under reduced pressure, the residue was neutralized with sodium sulfite solution under ice-cooling, pH 8, and the mixture was extracted with dichloromethane (100 mL×3). Organic layer was washed with brine solution (50 mL) and dried over Na$_2$SO$_4$ and the solvent was concentrated under vacuum to obtain the crude compound which was further purified by flash chromatography using n-hexane: ethyl acetate (97:3) to afford the title compound. Yield: 15 g (98.1%); $^1$H-NMR (CDCl$_3$, 400 MHz) δ ppm: 2.38 (s, 3H), 3.94 (s, 3H), 6.88 (s, 1H), 7.96 (s, 1H), 10.58 (s, 1H); Mass (m/z): 244.8 (M+H)$^+$.

Intermediate 15: Methyl 5-bromo-2-hydroxy-4-methyl-3-nitrobenzoate (I-15)

To a mixture of methyl 5-bromo-2-hydroxy-4-methyl-benzoate (13.3 g, 0.05 mol) in H$_2$SO$_4$ (60 mL) was added KNO$_3$ (8.2 g, 0.08 mol) at 0° C. and the mixture was stirred at room temperature for 3 h. The reaction mixture was poured into 1000 mL of chilled water during which solids precipitated. These solids were filtered and dissolved in CH$_2$Cl$_2$ (500 mL). The organic layer was washed with brine (250 mL), dried over anhydrous Na$_2$SO$_4$, filtered and concentrated on rotavap to obtain crude mass of the title compound.

Yield: 13.9 g; $^1$H-NMR (CDCl$_3$, 400 MHz) δ ppm: 2.39 (s, 3H), 3.98 (s, 3H), 8.12 (s, 1H), 11.14 (s, 1H); Mass (m/z): 290.0 (M+H)$^+$.

Intermediate 16: Methyl 2-hydroxy-4-methyl-3-nitro-5-(4,4,5,5-tetramethyl-[1,3,2]dioxaborolan-2-yl)-benzoate (I-16)

To a solution of methyl 5-bromo-2-hydroxy-4-methyl-3-nitro-benzoate (0.1 g, 0.0003 mol) in 1,4-dioxane (10 mL) in a sealed tube under N$_2$ at 25° C., was added potassium acetate (0.101 g, 0.001 mol), bis(pinacolato)diboron (0.131 g, 0.0005 mol) and 1,1-bis(diphenylphosphino)ferrocenepalladium(II)dichloride dichloromethane complex (0.028 g, 0.00003 mol). The reaction mixture was heated at 100° C. for 16 h, cooled to RT, filtered through a pad of celite and washed with ethylacetate (20 mL×2). The filtrate was concentrated under vacuum to obtain the crude of the title compound.

Yield: 1.4 g; Mass (m/z): 336.2 (M+H)$^-$.

Intermediate 17: Methyl 2-hydroxy-4-methyl-5-[4-(1-methyl-1H-pyrazol-4-yl)-benzyl]-3-nitrobenzoate (I-17)

To a solution of methyl 2-hydroxy-4-methyl-3-nitro-5-(4,4,5,5-tetramethyl-[1,3,2]dioxaborolan-2-yl)-benzoate (1.5 g, 0.004 mol) in a mixture of 100 mL of THF and 10 mL of water under N$_2$, was added 2-Hydroxy-4-methyl-3-nitro-5-(4,4,5,5-tetramethyl-[1,3,2]dioxaborolan-2-yl)-benzoic acid methyl ester (1.11 g, 0.004 mol), cesium carbonate (2.90 g, 0.008 mol) and [1,1'-bis(diphenylphosphino)ferrocene]dichloro-palladium (II), 1:1 complex with dichloromethane (0.369 g, 0.0004 mol). The mixture was refluxed for 7h, cooled to RT, filtered through celite, and washed with ethyl acetate (100 mL×2). The filtrate was concentrated under vacuum to obtain the crude compound which was further purified by flash chromatography using ethyl acetate: n-hexane (60:40) to obtain the title compound.

Yield: 0.196 g; $^1$H-NMR (CDCl$_3$, 400 MHz) δ ppm: 2.19 (s, 3H), 2.37 (s, 3H), 3.91-3.97 (m, 5H), 7.14-7.25 (d, J=8.1 Hz, 1H), 7.44 (s, 1H), 7.46-7.50 (m, 2H), 7.59 (s, 1H), 7.73-7.77 (m, 2H), 11.14 (s, 1H); Mass (m/z): 382.1 (M+H)$^+$.

Intermediate 18: Methyl 3-amino-2-hydroxy-4-methyl-5-[4-(1-methyl-1H-pyrazol-4-yl)-benzyl]-benzoate (I-18)

To a solution of methyl 2-hydroxy-4-methyl-5-[4-(1-methyl-1H-pyrazol-4-yl)-benzyl]-3-nitro-benzoate (0.196 g, 0.0005 mol) in methanol (20 mL) was added 10% palladium on carbon (0.109 g, 0.001 mol) and stirred under hydrogen atmosphere for 5 h and filtered the mass through celite and washed with methanol (50 mL). The filtrate was concentrated under vacuum to obtain the crude compound which was further purified by flash chromatography using ethyl acetate:hexane (60:40) to obtain the title compound.

Yield: 0.93 g; $^1$H-NMR (CDCl$_3$, 400 MHz) δ ppm: 2.04 (s, 3H), 3.84 (bs, 2H), 3.92 (s, 3H), 3.93 (s, 3H), 3.94 (s, 2H), 7.06-7.08 (d, J=7.9 Hz, 2H), 7.15 (s, 1H), 7.34-7.36 (d, J=8.04 Hz, 2H), 7.56 (s, 1H), 7.72 (s, 1H), 10.83 (s, 1H); Mass (m/z): 352.2 (M+H)$^+$.

Intermediate 19: Methyl 5-methyl-6-[4-(1-methyl-1H-pyrazol-4-yl)-benzyl]-3,4-dihydro-2H-benzo[1,4]oxazine-8-carboxylate (I-19)

Cs$_2$CO$_3$ (0.430 g, 0.001 mole) was added to a stirred solution of methyl 3-amino-2-hydroxy-4-methyl-5-[4-(1- methyl-1H-pyrazol-4-yl)-benzyl]-benzoate (0.93 g, 0.0026 mol), 1-bromo-2-chloroethane (0.06 mL, 0.007 mol) in DMF (2 mL). The reaction mixture was stirred at room temperature for 30 h, cooled to, poured on to water (50 mL) and extracted with ethyl acetate (50 mL×3). The organic extracts were combined, dried over anhydrous $Na_2SO_4$, filtered and concentrated on rotavap to obtain crude mass which was purified by column chromatography using methanol:dichloromethane (2:98) to obtain the title compound.

Yield: 0.99 g; Mass (m/z): 378.1 $(M+H)^+$.

Intermediate 20: Methyl 5-bromo-4-methyl-2-prop-2-ynyloxybenzoate (I-20)

To a stirred solution of methyl 5-bromo-2-hydroxy-4-methylbenzoate (0.75 g, 3.06 mmols), in acetonitrile (12.2 mL) at RT, $K_2CO_3$ (0.633 g, 4.60 mmol) and propargyl bromide (0.2 mL, 3.36 mmol) were added. The reaction mixture was stirred at reflux temperature for 16 h, cooled to RT, diluted with EtOAc and water. The two layers were separated and the aqueous layer was extracted with ethyl acetate. The organic extracts were combined, washed with brine solution, dried over anhydrous $Na_2SO_4$, filtered and concentrated under reduced pressure to obtain the title compound.

Yield: 0.85 g (98%); $^1$H-NMR (400 MHz, DMSO): δ 7.82 (s, 1H), 7.26 (s, 1H), 4.89 (s, 2H), 3.78 (s, 3H), 3.62 (s, 1H), 2.38 (s, 3H); Mass (m/z): 283.0, 285.0 $(M+H)^+$.

Intermediate 21: Methyl 5-bromo-2,4-dimethylbenzofuran-7-carboxylate (I-21)

Methyl 5-bromo-4-methyl-2-prop-2-ynyloxybenzoate (0.85 g, 3.0 mmol), in N-methylpyrrolidinone (1.49 mL) heated between 202° C. to 205° C. for 18 h. The reaction mixture was cooled to 0° C., and quenced by adding ice water mixture. The reaction mixture was diluted with EtOAc and the two layers were separated and the aqueous layer was extracted with ethyl acetate. The organic extracts were combined, washed with brine solution, dried over anhydrous $Na_2SO_4$, filtered and concentrated under reduced pressure to obtain the title compound as off white solid.

Yield: 0.3 g (35%); $^1$H-NMR (400 MHz, CDCl$_3$): δ 8.02 (s, 1H), 6.43 (s, 1H), 3.98 (s, 3H), 2.53 (s, 6H); Mass (m/z): 282.6, 284.9 $(M+H)^+$.

Example 1

N-(cis-1S,2S-2-Hydroxycyclohexyl)-6-(2-chloropyridin-4-ylmethyl)-5-methylquinoline-8-carboxamide

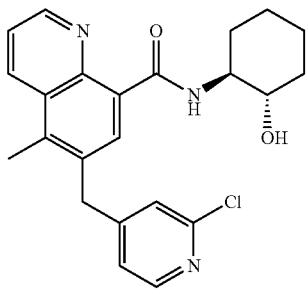 [SMILES: Cc1c(Cc2ccnc(Cl)c2)cc(C(=O)N[C@H]2CCCC[C@@H]2O)c2ncccc12]

Step 1: Synthesis of methyl 6-(2-chloropyridin-4-ylmethyl)-5-methylquinoline-8-carboxylate To a stirred solution of methyl 6-bromo-5-methylquinoline-8-carboxylate (I-2), (0.25 g, 0.89 mmol) in 1,4-dioxane (5.9 mL) cooled at RT, potassium acetate (0.27 g, 3.1 mmol) and bis(pinacolato)diboron (0.34 g, 1.33 mmol) were added. Reaction mixture was degassed with nitrogen for 15 minutes and [1,1'-bis(diphenylphosphino)ferrocene] palladium(II) dichloride (72.8 mg, 0.08 mmol) was added. The reaction mixture was gradually heated to 100° C. and was stirred at this temperature for 10 h. After cooling it to RT, the volatiles were removed under reduced pressure. The crude product obtained was dissolved in 4:1 mixture of 1,4-dioxane and water (5.9 mL). Solid $K_2CO_3$ (0.16 g, 1.14 mmol) and 2-chloro-4-chloromethyl-pyridine (0.19 g, 1.15 mmol) were added. The reaction mixture was degassed with nitrogen for 15 minutes and [1,1'-bis(diphenylphosphino)ferrocene]palladium(II) dichloride (62.3 mg, 0.07 mmol) was added. The reaction mixture was gradually heated to 100° C. and was stirred at this temperature for 8 h. After cooling it to RT, the volatiles were removed under reduced pressure and the crude boronate ester was dissolved in water and EtOAc. The reaction mass was filtered through celite bed and the two layers were separated. The aqueous layer was extracted with EtOAc. The combined organic layer was washed once with brine solution, dried over anhydrous $Na_2SO_4$ and the solvent was removed under reduced pressure to obtain a crude product which was purified by silica gel column chromatography to obtain the title compound.

Yield: 111 mg (40%); $^1$H-NMR (400 MHz, CDCl$_3$): δ 9.07 (d, J=4.0 Hz, 1H), 8.44 (d, J=8.6 Hz, 1H), 8.28 (d, J=5.0 Hz, 1H), 7.86 (s, 1H), 7.53 (dd, J=4.0, 8.6 Hz, 1H), 7.06 (s, 1H), 6.97 (d, J=4.9 Hz, 1H), 4.23 (s, 2H), 4.04 (s, 3H), 2.58 (s, 3H); Mass (m/z): 327.2, 328.9 $(M+H)^+$.

Step 2: Synthesis of 6-(2-chloropyridin-4-ylmethyl)-5-methylquinoline-8-carboxylic acid To a stirred solution of methyl 6-(2-chloropyridin-4-ylmethyl)-5-methylquinoline-8-carboxylate obtained in step 1 (0.11 g, 0.34 mmol) in 1:1 mixture of $H_2O$ and methanol (2.0 mL) cooled at 0° C., solid NaOH (0.04 g, 1.01 mmol) was added. After stirring for 2 h at reflux temperature, the reaction mixture was cooled to RT, acidified with 2N HCl and extracted with DCM. The combined organic layer was washed once with brine solution, dried over anhydrous $Na_2SO_4$ and the solvent was removed under reduced pressure to obtain the title compound.

Yield: 0.11 g (100%); $^1$H-NMR (400 MHz, CDCl$_3$): δ 16.65 (bs, 1H), 8.94 (d, J=3.2 Hz, 1H), 8.68 (s, 1H), 8.65 (d, J=8.7 Hz, 1H), 8.29 (d, J=5.1 Hz, 1H), 7.68 (dd, J=4.3, 8.6 Hz, 1H), 7.04 (s, 1H), 6.99 (d, J=4.9 Hz, 1H) 4.29 (s, 2H), 2.65 (S, 3H); Mass (m/z): 312.9, 314.9 $(M+H)^+$.

Step 3: Synthesis of N-(cis-1S,2S-2-hydroxycyclohexyl)-6-(2-chloropyridin-4-ylmethyl)-5-methylquinoline-8-carboxamide To a stirred solution of 6-(2-chloropyridin-4-ylmethyl)-5-methylquinoline-8-carboxylic acid, (114 mg, 0.34 mmol) in DCM (3.4 mL) cooled at 0° C., DIPEA (0.18 mL, 1.1 mmol), cis 2-aminocyclohexanol hydrochloride (50.6 mg, 0.43 mmol) and TBTU (151.6 mg, 0.40 mmol) in sequence were added. After stirring for 16 hours at RT, the reaction mixture was diluted with water and DCM. The two layers were separated and aqueous layer was extracted with DCM.

The combined organic layer was washed once with brine solution, dried over anhydrous Na₂SO₄ and the solvent was removed under reduced pressure to obtain a crude product which was purified by silica gel column chromatography to obtain the title compound.

Yield: 90.0 mg (64%); ¹H-NMR (400 MHz, CDCl₃): δ 11.52 (bs, 1H), 8.92 (d, J=4.1 Hz, 1H), 8.7 (s, 1H), 8.53 (d, J=8.6 Hz, 1H), 8.26 (d, J=5.12 Hz, 1H), 7.56 (dd, J=4.1 Hz, 8.6 Hz, 1H), 7.03 (s, 1H), 6.98 (s J=5.08 Hz, 1H), 4.39 (bs, 1H), 4.28 (s, 2H), 4.00-3.94 (m, 1H), 3.64-3.50 (m, 1H), 2.58 (s, 3H), 2.17-2.13 (m, 2H), 1.81-1.78 (m, 2H), 1.48-1.45 (m, 4H); Mass (m/z): 410.1, 412.1 (M+H)⁺.

The following examples were synthesized by following the experimental procedure as described in the preparation of Example 1 using the appropriate intermediate, I-2 with some non-critical variation.

| Example No. | Structure and IUPAC name | Characterization data |
| --- | --- | --- |
| Example 2 | 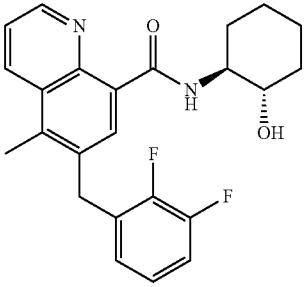 [SMILES: Cc1c(Cc2cccc(F)c2F)cc(C(=O)N[C@H]2CCCC[C@@H]2O)c2ncccc12]<br>N-(cis-1S,2S-2-Hydroxycyclohexyl)-6-(2,3-difluorobenzyl)-5-methylquinoline-8-carboxamide | ¹H-NMR (400 MHz, CDCl₃): δ 11.51 (bs, 1H), 8.89 (d, J = 3.92 Hz, 1H), 8.70 (s, 1H), 8.53 (d, J = 7.4 Hz, 1H), 7.53 (dd, J = 4.2 Hz, 8.6 Hz, 1H), 7.02 (dd, J = 8.5 Hz, 17.2 Hz, 1H), 6.93 (dd, J = 7.9 Hz, 13.1 Hz, 1H), 6.68 (t, J = 6.8 Hz, 1H), 4.45 (bs, 1H), 4.30 (bs, 2H), 3.99-3.96 (m, 1H), 3.62-3.59 (m, 1H), 2.63 (s, 3H), 2.16-2.12 (m, 2H), 1.76-1.80 (m, 2H), 1.50-1.45 (m, 4H); Mass (m/z): 411.1 (M + H)⁺. |
| Example 3 | 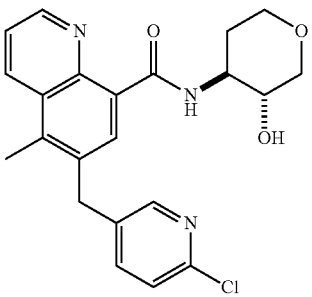<br>N-(cis-3S,4S-3-Hydroxytetrahydropyran-4-yl)-6-(2-chloropyridin-5-ylmethyl)-5-methylquinoline-8-carboxamide | ¹H-NMR (400 MHz, CDCl₃): δ 11.78 (bs, 1H), 8.91 (d, J = 7.4 Hz, 1H), 8.72 (s, 1H), 8.54 (d, J = 8.3 Hz, 1H), 8.25 (s, 1H), 7.57 (dd, J = 3.8 Hz, 8.2 Hz, 1H), 7.36 (d, J = 7.4 Hz, 1H), 7.22 (d, J = 8.2 Hz, 1H), 5.07 (bs, 1H), 4.27 (s, 2H), 4.13-4.11 (m, 3H), 3.73-3.72 (m, 1H), 3.65-3.52 (m, 1H), 3.3-3.25 (m, 1H), 2.62 (s, 3H), 2.15-2.12 (m, 1H), 1.99-1.90 (m, 1H); Mass (m/z): 412.1, 414.2 (M + H)⁺. |
| Example 4 | 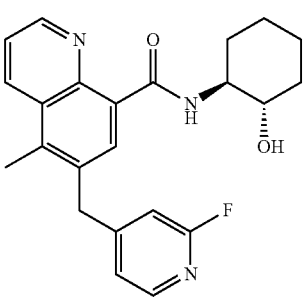 [SMILES: Cc1c(Cc2ccnc(F)c2)cc(C(=O)N[C@H]2CCCC[C@@H]2O)c2ncccc12]<br>N-(cis-1S,2S-2-Hydroxycyclohexyl)-6-(2-fluoropyridin-4-ylmethyl)-5-methylquinoline-8-carboxamide | ¹H-NMR (400 MHz, CDCl₃): δ 11.50 (bs, 1H), 8.92 (d, J = 3.6 Hz, 1H), 8.71 (s, 1H), 8.54 (d, J = 8.5 Hz, 1H), 8.10 (d, J = 4.8 Hz, 1H), 7.57 (dd, J = 4.0 Hz, 8.4 Hz, 1H), 7.00 (d, J = 16.14 Hz, 1H), 6.62 (s, 1H), 4.37 (bs, 1H), 4.32 (s, 2H), 4.00-3.97 (m, 1H), 3.64-3.59 (m, 1H), 2.59 (s, 3H), 2.20-2.16 (m, 2H), 1.85-1.75 (m, 2H), 1.40-1.26 (m, 4H); Mass (m/z): 394.0 (M + H)⁺. |

-continued

| Example No. | Structure and IUPAC name | Characterization data |
|---|---|---|
| Example 5 | 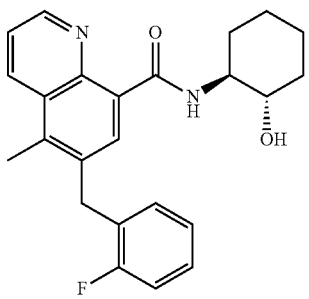 [SMILES: Cc1c(Cc2ccccc2F)cc(C(=O)N[C@H]2CCCC[C@@H]2O)c2ncccc12]<br>N-(cis-1S,2S-2-Hydroxycyclohexyl)-6-(2-fluorobenzyl)-5-methylquinoline-8-carboxamide | $^1$H-NMR (400 MHz, CDCl$_3$): δ 11.51 (bs, 1H), 8.88 (d, J = 3.9 Hz, 1H), 8.72 (s, 1H), 8.53 (d, J = 8.64 Hz, 1H), 7.52 (dd, J = 4.1 Hz, 8.6 Hz, 1H), 7.25-7.15 (m, 1H), 7.07 (t, J = 9.3 Hz, 1H), 6.99 (t, J = 7.3 Hz, 1H), 6.92 (t, J = 7.1 Hz, 1H), 4.50 (bs, 1H), 4.28 (bs, 2H), 4.03-3.93 (m, 1H), 3.612-3.52 (m, 1H), 2.63 (s, 3H), 2.2-2.10 (m, 2H), 1.85-1.75 (m, 2H), 1.50-1.30 (m, 4H); Mass (m/z): 392.9 (M + H)$^+$. |
| Example 6 | 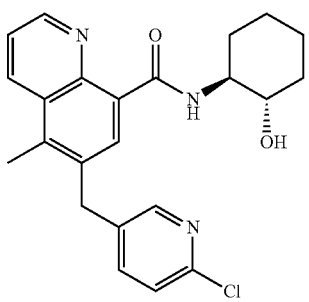 [SMILES: Cc1c(Cc2ccc(Cl)nc2)cc(C(=O)N[C@H]2CCCC[C@@H]2O)c2ncccc12]<br>N-(cis-1S,2S-2-Hydroxycyclohexyl)-6-(2-chloropyridin-5-ylmethyl)-5-methylquinoline-8-carboxamide | $^1$H-NMR (400 MHz, CDCl$_3$): δ 11.51 (bs, 1H), 8.90 (d, J = 3.0 Hz, 1H), 8.70 (s, 1H), 8.52 (d, J = 8.4 Hz, 1H), 8.25 (s, 1H), 7.55 (dd, J = 4.0 Hz, 8.5 Hz, 1H), 7.35 (d, J = 6.0 Hz, 1H), 7.21 (d, J = 8.3 Hz, 1H), 4.40 (bs, 1H), 4.26 (s, 2H), 4.0-3.91 (m, 1H), 3.62-3.55 (m, 1H), 2.63 (s, 3H), 2.2-2.10 (m, 2H), 1.82-1.73 (m, 2H), 1.38-1.23 (m, 4H); Mass (m/z): 410.0, 412.1 (M + H)$^+$. |
| Example 7 | 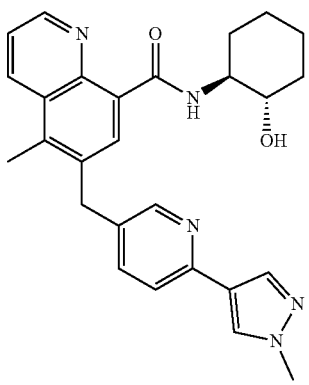 [SMILES: Cc1c(Cc2ccc(-c3cnn(C)c3)nc2)cc(C(=O)N[C@H]2CCCC[C@@H]2O)c2ncccc12]<br>N-(cis-1S,2S-2-Hydroxycyclohexyl)-6-[2-(1-methyl-1H-pyrazol-4-yl)-pyridin-5-ylmethyl]-5-methylquinoline-8-carboxamide | $^1$H-NMR (400 MHz, CDCl$_3$): δ 11.51 (d, J = 6.3 Hz, 1H), 8.89 (s, 1H), 8.75 (s, 1H), 8.51 (d, J = 8.7 Hz, 1H), 8.39 (s, 1H), 7.88 (s, 1H), 7.86 (s, 1H), 7.53 (dd, J = 4.1, 8.6 Hz, 1H), 7.40-7.30 (m, 2H), 4.47 (bs, 1H), 4.27 (s, 2H), 4.04-3.90 (m, 1H), 3.93 (s, 3H), 3.64-3.50 (m, 1H), 2.63 (s, 3H), 2.17-2.13 (m, 2H), 1.81-1.78 (m, 2H), 1.48-1.45 (m, 4H); Mass (m/z): 456.1 (M + H)$^+$. |

-continued

| Example No. | Structure and IUPAC name | Characterization data |
|---|---|---|
| Example 8 | 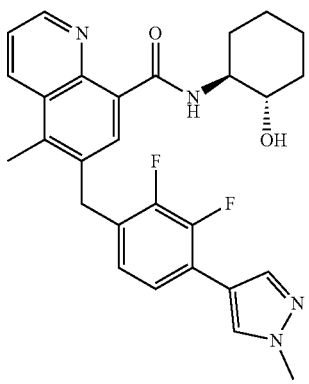 [SMILES: Cc1c(Cc2ccc(-c3cnn(C)c3)c(F)c2F)cc(C(=O)N[C@H]2CCCC[C@@H]2O)c2ncccc12]<br>N-(cis-1S,2S-2-Hydroxycyclohexyl)-6-[2,3-difluoro-4-(1-methyl-1H-pyrazol-4-yl)-benzyl]-5-methylquinoline-8-carboxamide | $^1$H-NMR (400 MHz, CDCl$_3$): δ 11.52 (bs, 1H), 8.89 (d, J = 3.6 Hz, 1H), 8.72 (s, 1H), 8.53 (d, J = 8.5 Hz, 1H), 7.77 (s, 1H), 7.73 (s, 1H), 7.53 (dd, J = 4.1, 8.4 Hz, 1H), 7.13 (d, J = 7.6 Hz, 1H), 6.68 (d, J = 7.4 Hz, 1H), 4.46 (bs, 1H), 4.29 (s, 2H), 3.99-3.97 (m, 1H), 3.95 (s, 3H), 3.62-3.58 (m, 1H), 2.65 (s, 3H), 2.29-2.18 (m, 2H), 1.82-1.78 (m, 2H), 1.45-1.35 (m, 4H); Mass (m/z): 491.0 (M + H)$^+$. |
| Example 9 | 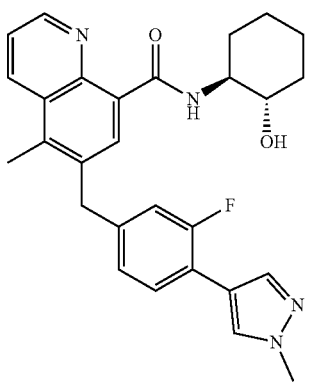 [SMILES: Cc1c(Cc2ccc(-c3cnn(C)c3)c(F)c2)cc(C(=O)N[C@H]2CCCC[C@@H]2O)c2ncccc12]<br>N-(cis-1S,2S-2-Hydroxycyclohexyl)-6-[3-fluoro-4-(1-methyl-1H-pyrazol-4-yl)-benzyl]-5-methylquinoline-8-carboxamide | $^1$H-NMR (400 MHz, CDCl$_3$): δ 11.79 (bs, 1H), 8.74 (d, J = 7.6 Hz, 1H), 8.66 (s, 1H), 8.33 (d, J = 8.5 Hz, 1H), 7.84 (s, 1H), 7.77 (s, 1H), 7.60-7.49 (m, 1H), 7.43 (dd, J = 4.1, 8.6 Hz, 1H), 7.19-7.08 (m, 2H), 5.61 (bs, 1H), 4.83 (s, 2H), 4.03-3.98 (m, 1H), 3.96 (s, 3H), 3.70-3.58 (m, 1H), 2.80 (s, 3H), 2.25-2.18 (m, 2H), 1.81-1.70 (m, 2H), 1.43-1.32 (m, 4H); Mass (m/z): 473.1 (M + H)$^+$. |
| Example 10 | 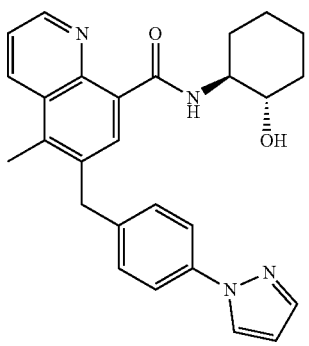 [SMILES: Cc1c(Cc2ccc(-n3cccn3)cc2)cc(C(=O)N[C@H]2CCCC[C@@H]2O)c2ncccc12]<br>N-(cis-1S,2S-2-Hydroxycyclohexyl)-6-(4-pyrazol-1-yl-benzyl)-5-methylquinoline-8-carboxamide | $^1$H-NMR (400 MHz, CDCl$_3$): δ 11.52 (bs, 1H), 8.89 (d, J = 3.6 Hz, 1H), 8.75 (s, 1H), 8.53 (d, J = 8.5 Hz, 1H), 7.86 (s, 1H), 7.69 (s, 1H), 7.61-7.52 (m, 4H), 7.21 (s, 1H), 7.18 (s, 1H), 6.43 (s, 1H), 4.46 (bs, 1H), 4.32 (s, 2H), 3.99-3.96 (m, 1H), 2.62 (s, 3H), 2.18-2.12 (m, 2H), 1.93-1.79 (m, 2H), 1.42-1.30 (m, 4H); Mass (m/z): 441.1 (M + H)$^+$. |

| Example No. | Structure and IUPAC name | Characterization data |
|---|---|---|
| Example 11 | 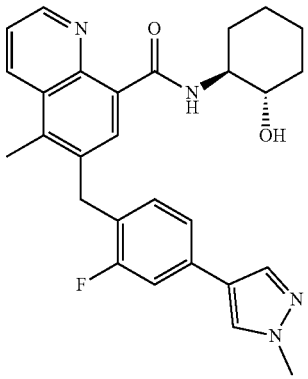 [SMILES: Cc1c(Cc2ccc(-c3cnn(C)c3)cc2F)cc(C(=O)N[C@H]2CCCC[C@@H]2O)c2ncccc12]<br>N-(cis-1S,2S-2-Hydroxycyclohexyl)-6-[2-fluoro-4-(1-methyl-1H-pyrazol-4-yl)-benzyl]-5-methylquinoline-8-carboxamide | $^1$H-NMR (400 MHz, CDCl$_3$): δ 11.50 (bs, 1H), 8.88 (d, J = 4.4 Hz, 1H), 8.73 (s, 1H), 8.54 (d, J = 8.5 Hz, 1H), 7.69 (s, 1H), 7.50 (s, 1H), 7.54 (dd, J = 4.1, 8.6 Hz, 1H), 7.16-7.08 (m, 2H), 6.91 (d, J = 2.4 Hz, 1H), 4.50 (bs, 1H), 4.27 (s, 2H), 4.04-3.95 (m, 1H), 3.92 (s, 3H), 3.65-3.55 (m, 1H), 2.65 (s, 3H), 2.25-2.18 (m, 2H), 1.85-1.70 (m, 2H), 1.56-1.42 (m, 4H); Mass (m/z): 473.1 (M + H)$^+$. |
| Example 12 | 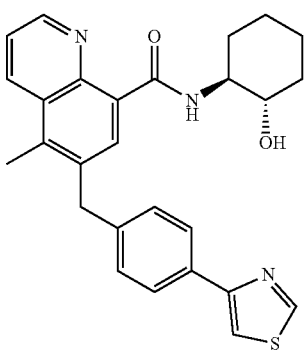 [SMILES: Cc1c(Cc2ccc(-c3cscn3)cc2)cc(C(=O)N[C@H]2CCCC[C@@H]2O)c2ncccc12]<br>N-(cis-1S,2S-2-Hydroxycyclohexyl)-6-(4-thiazol-4-yl-benzyl)-5-methylquinoline-8-carboxamide | $^1$H-NMR (400 MHz, CDCl$_3$): δ 11.54 (bs, 1H), 8.88 (d, J = 3.0 Hz, 1H), 8.85 (s, 1H), 8.77 (s, 1H), 8.52 (d, J = 8.2 Hz, 1H), 7.82 (d, J = 8.0 Hz, 2H), 7.52 (dd, J = 3.7, 8.4 Hz, 1H), 7.47 (s, 1H), 7.20 (d, J = 8.0 Hz, 2H), 4.54 (bs, 1H), 4.32 (s, 2H), 4.12-3.91 (m, 1H), 3.65-3.52 (m, 1H), 2.65 (s, 3H), 2.20-2.11 (m, 2H), 1.84-1.73 (m, 2H), 1.48-1.36 (m, 4H); Mass (m/z): 458.2 (M + H)$^+$. |
| Example 13 | 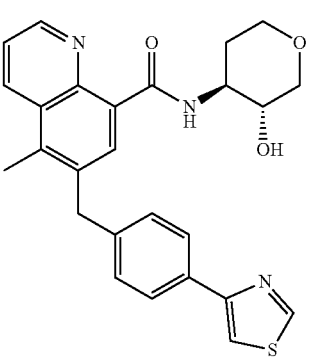 [SMILES: Cc1c(Cc2ccc(-c3cscn3)cc2)cc(C(=O)N[C@H]2CCOC[C@@H]2O)c2ncccc12]<br>N-(cis-3S,4S-3-Hydroxytetrahydro-pyran-4-yl)-6-(4-thiazol-4-yl-benzyl)-5-methylquinoline-8-carboxamide | $^1$H-NMR (400 MHz, CDCl$_3$): δ 11.83 (bs, 1H), 8.89 (d, J = 3.1 Hz, 1H), 8.85 (s, 1H), 8.75 (s, 1H), 8.54 (d, J = 8.4 Hz, 1H), 7.83 (d, J = 8.0 Hz, 2H), 7.54 (dd, J = 4.1, 8.6 Hz, 1H), 7.47 (s, 1H), 7.22 (d, J = 8.0 Hz, 2H), 5.21 (bs, 1H), 4.33 (s, 2H), 4.29-4.13 (m, 2H), 4.11-4.0 (m, 1H), 3.78-3.69 (m, 1H), 3.55-3.48 (m, 2H), 2.64 (s, 3H), 2.19 (m, 1H), 2.0-1.93 (m, 1H); Mass (m/z): 460.1 (M + H)$^+$. |

| Example No. | Structure and IUPAC name | Characterization data |
|---|---|---|
| Example 14 | 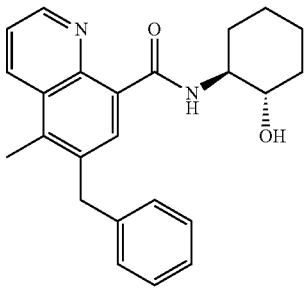 [SMILES: Cc1c(Cc2ccccc2)cc(C(=O)N[C@H]2CCCC[C@@H]2O)c2ncccc12]<br>N-(cis-1S,2S-2-Hydroxycyclohexyl)-6-benzyl-5-methylquinoline-8-carboxamide | $^1$H-NMR (300 MHz, CDCl$_3$): δ 11.55 (d, J = 6.0 Hz, 1H), 8.87 (d, J = 3.2 Hz, 1H), 8.75 (s, 1H), 8.52 (d, J = 8.4 Hz, 1H), 7.52 (dd, J = 3.7, 8.4 Hz, 1H), 7.24 (d, J = 6.9 Hz, 2H), 7.19 (d, J = 6.9 Hz, 1H), 7.13 (d, J = 6.9 Hz, 2H), 4.57 (bs, 1H), 4.29 (s, 2H), 4.12-3.91 (m, 1H), 3.65-3.52 (m, 1H), 2.62 (s, 3H), 2.20-2.11 (m, 2H), 1.84-1.73 (m, 2H), 1.48-1.36 (m, 4H); Mass (m/z): 375.2 (M + H)$^+$. |
| Example 15 | 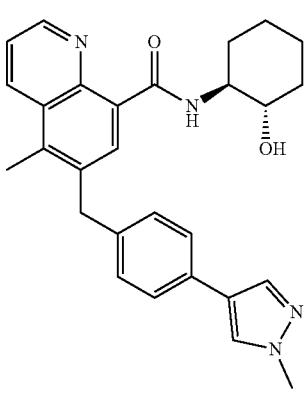 [SMILES: Cc1c(Cc2ccc(-c3cnn(C)c3)cc2)cc(C(=O)N[C@H]2CCCC[C@@H]2O)c2ncccc12]<br>N-(cis-1S,2S-2-Hydroxycyclohexyl)-6-[4-(1-methyl-1H-pyrazol-4-yl)-benzyl]-5-methylquinoline-8-carboxamide | $^1$H-NMR (400 MHz, CDCl$_3$): δ 11.51 (bs, 1H), 8.87 (d, J = 4.4 Hz, 1H), 8.76 (s, 1H), 8.51 (d, J = 8.8 Hz, 1H), 7.69 (s, 1H), 7.54 (s, 1H), 7.54 (s, 1H), 7.51 (dd, J = 4.4, 8.8 Hz, 1H), 7.35 (d, J = 8.0 Hz, 2H), 7.12 (d, J = 8.0 Hz, 2H), 4.50 (bs, 1H), 4.28 (s, 2H), 4.03-3.92 (m, 1H), 3.91 (s, 3H), 3.65-3.57 (m, 1H), 2.64 (s, 3H), 2.20-2.10 (m, 2H), 1.83-1.75 (m, 2H), 1.60-1.25 (m, 4H); Mass (m/z): 455.1 (M + H)$^+$. |

The Examples 16 and 17 were prepared by following the experimental procedure as described in the preparation of Example 1 using the appropriate intermediate, I-19 with some non-critical variation.

| Example No. | Structure and IUPAC name | Characterization data |
|---|---|---|
| Example 16 | 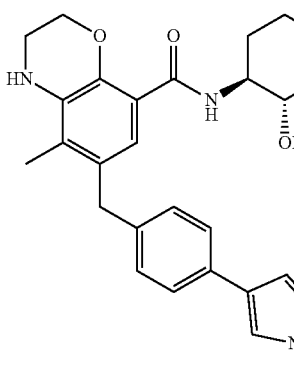<br>N-(cis-1S,2S-2-Hydroxycyclohexyl)-6-[4-(1-methyl-1H-pyrazol-4-yl)-benzyl]-5-methyl-3,4-dihydro-2H-benzo[1,4]oxazine-8-carboxamide | $^1$H-NMR (DMSO-d$_6$, 400 MHz) δ ppm: 1.15-1.18 (m, 4H), 1.56-1.64 (m, 2H), 1.83-1.85 (m, 1H), 1.93 (s, 3H), 1.99-2.02 (m, 1H), 3.19-3.21 (m, 2H), 3.56-3.60 (m, 2H), 3.84 (s, 3H), 3.86 (s, 2H), 4.21 (m, 2H), 4.69-4.71 (d, J = 5.2 Hz, 1H), 5.31 (s, 1H), 7.00 (s, 1H), 7.04-7.06 (d, J = 7.8 Hz, 2H), 7.41-7.43 (d, J = 7.90 Hz, 2H), 7.77 (s, 1H), 7.96-7.97 (d, J = 7.04 Hz, 1H), 8.04 (s, 1H); Mass (m/z): 460.9 (M + H)$^+$. |

| Example No. | Structure and IUPAC name | Characterization data |
|---|---|---|
| Example 17 | 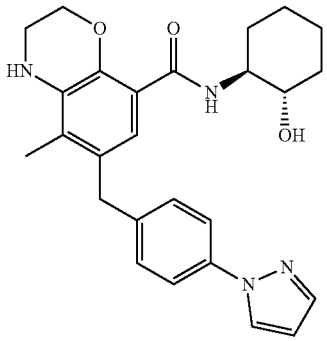 [SMILES: Cc1c(Cc2ccc(-n3cccn3)cc2)cc(C(=O)N[C@H]2CCCC[C@@H]2O)c2c1NCCO2]<br>N-(cis-1S,2S-2-Hydroxycyclohexyl)-6-(4-pyrazol-1-yl-benzyl)-5-methyl-3,4-dihydro-2H-benzo[1,4]oxazine-8-carboxamide | $^1$H-NMR (DMSO-d$_6$, 400 MHz) δ ppm: 1.22-1.24 (m, 4H), 1.55-1.62 (m, 2H), 1.82-1.83 (m, 2H), 1.92 (s, 3H), 2.82-2.84 (m, 2H), 3.34 (s, 3H), 3.54-3.55 (m, 2H), 3.90 (s, 2H), 4.19 (s, 2H), 6.50 (s, 1H), 7.00 (s, 1H), 7.17-7.19 (d, J = 8.3 Hz, 2H), 7.65-7.69 (m, 3H), 8.34 (s, 1H); Mass (m/z): 447.2 (M + H)$^+$. |

Example 18: N-(cis-1S,2S-2-Hydroxycyclohexyl)-5-methyl-6-[4-(1-methyl-1H-pyrazol-4-yl)-benzyl]-imidazo[1,2-a]pyridine-8-carboxamide

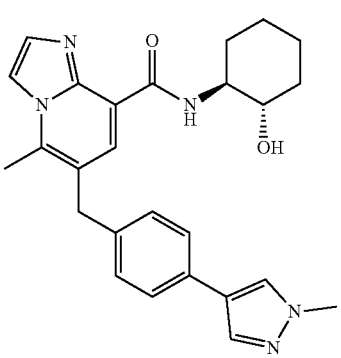

Step 1: Synthesis of 5-methyl-6-[4-(1-methyl-1H-pyrazol-4-yl)-benzyl]-imidazo[1,2-a]pyridine-8-carbonitrile To a stirred solution of 6-bromo-5-methyl-imidazo[1,2-a]pyridine-8-carbonitrile (I-6) (0.1 g, 0.42 mmol) in toluene (5.9 mL) at RT, potassium acetate (0.14 g, 1.43 mmol) and bis(pinacolato)diboron (0.16 g, 0.63 mmol) were added. The reaction mixture was degassed with nitrogen for 15 minutes and [1,1'-bis(diphenypenylphosphino)frrocene] palladium (II) dichloride (17.0 r mg, 0.02 mmol) was added. The reaction mixture was gradually heated to 100° C. and was stirred at this temperature for 20 h. After cooling it to RT, the crude product in toluene was diluted with 9:1 mixture of 1,4-dioxane and water (3.7 mL). Solid K$_2$CO$_3$ (0.07 g, 0.5 mmol) and 4-(4-chloromethyl-phenyl)-1-methyl-1H-pyrazole (0.07 g, 0.35 mmol) were added. The reaction mixture was degassed with nitrogen for 15 minutes and [1,1'-bis(diphenylphosphino)ferrocene] palladium(II) dichloride (28.0 mg, 0.04 mmol) was added. The reaction mixture was gradually heated to 100° C. and was stirred at this temperature for 6 h. After cooling it to RT, the volatiles were removed under reduced pressure and the crude product was dissolved in water and EtOAc. The reaction mass was filtered through celite bed and the two layers were separated. The aqueous layer was extracted with EtOAc. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 40 mg (35%); $^1$H-NMR (400 MHz, CDCl$_3$): δ 7.82 (s, 1H), 7.73 (s, 1H), 7.61 (s, 1H), 7.59 (s, 1H), 7.54 (s, 1H), 7.42 (d, J=8.04 Hz, 2H), 7.10 (d, J=8.00 Hz, 2H), 4.07 (s, 2H), 3.94 (s, 3H), 2.66 (s, 3H); Mass (m/z): 328.1 (M+H)$^+$.

Step 2: Synthesis of 5-methyl-6-[4-(1-methyl-1H-pyrazol-4-yl)-benzyl]-imidazo[1,2-a]pyridine-8-carboxamide To a stirred solution of 5-methyl-6-[4-(1-methyl-1H-pyrazol-4-yl)-benzyl]-imidazo[1,2-a]pyridine-8-carbonitrile obtained in step 1 (0.02 g, 0.06 mmol) in 1:1 mixture of H$_2$O and ethanol (1.0 mL) at RT, solid KOH (0.009 g, 0.15 mmol) was added. After stirring for 3 h at 85° C., the reaction mixture was cooled to RT, the volatiles were removed under reduced pressure to obtain the title compound.

Yield: 0.02 g (95%); $^1$H-NMR (400 MHz, DMSO): δ 8.05 (s, 1H), 7.77 (s, 1H), 7.70 (d, J=8.2 Hz, 1H), 7.51 (d, J=5.9 Hz, 1H), 7.45 (d, J=8.1 Hz, 2H), 7.21 (d, J=8.1 Hz, 2H), 6.88 (s, 1H), 4.96 (s, 2H), 3.98 (s, 3H), 2.86 (s, 3H); Mass (m/z): 346.1 (M+H)$^+$.

Step 3: Synthesis of 5-methyl-6-[4-(1-methyl-1H-pyrazol-4-yl)-benzyl]-imidazo[1,2-a]pyridine-8-carboxylic acid To a stirred solution of 5-methyl-6-[4-(1-methyl-1H-pyrazol-4-yl)-benzyl]-imidazo[1,2-a]pyridine-8-carboxamide obtained in step 2 (0.02 g, 0.06 mmol) aq. HCl (5N, 1.0 mL) was added. After stirring for 6 h at 100° C., the reaction mixture was cooled to RT, the reaction mixture was basified with aq. Ammonia solution. The crude product was extracted with 9:1 mixture of DCM and methanol to obtain the title compound.

Yield: 0.02 g (100%); $^1$H-NMR (400 MHz, DMSO): δ 8.49 (s, 1H), 8.40 (s, 1H), 8.24 (s, 1H) 8.09 (d, J=4.5 Hz, 1H), 7.82 (d, J=4.5 Hz, 1H), 7.50 (d, J=7.6 Hz, 2H), 7.24 (d, J=7.6 Hz, 2H), 6.86 (s, 1H), 4.19 (s, 2H), 3.99 (s, 3H), 2.84 (s, 3H); Mass (m/z): 347.1 (M+H)$^+$.

Step 4: Synthesis of N-(cis-1S,2S-2-hydroxycyclohexyl)-5-methyl-6-[4-(1-methyl-1H-pyrazol-4-yl)-benzyl]-imidazo[1,2-a]pyridine-8-carboxamide To a stirred solution of 5-methyl-6-[4-(1-methyl-1H-pyrazol-4-yl)-benzyl]-imidazo[1,2-a]pyridine-8-carboxylic acid obtained in step 3 (20.0 mg, 0.06 mmol) in DCM (1.0 mL) cooled at 0° C., DIPEA (0.02 mL, 0.15 mmol), cis 2-aminocyclohexanol hydrochloride (8.7 mg, 0.06 mmol) and HATU (24.1 mg, 0.063 mmol) in sequence were added. After stirring for 1 h at RT, the reaction mixture was diluted with water and DCM.

The two layers were separated and aqueous layer was extracted with DCM. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 18.0 mg (72%); $^1$H-NMR (400 MHz, CDCl$_3$): δ 10.44 (d, J=6.2 Hz, 1H), 8.05 (s, 1H), 7.44 (s, 1H), 7.70 (d, J=8.2 Hz, 1H), 7.51 (d, J=5.96 Hz, 2H), 7.45 (d, J=8.16 Hz, 2H), 7.21 (d, J=6.6 Hz, 2H), 4.96 (s, 2H), 3.98 (s, 3H); 3.97-3.90 (m, 1H), 3.62-3.56 (m, 1H), 2.86 (s, 3H); 2.18-2.08 (m, 2H), 1.77-1.75 (m, 2H), 1.41-1.43 (m, 4H); Mass (m/z): 444.1 (M+H)$^+$.

The following Example 19 to Example 26 were synthesized by following the experimental procedure as described in the preparation of Example 18 using the appropriate intermediate, I-6 with some non-critical variation.

| Example No. | Structure and IUPAC Name | Characterization data |
|---|---|---|
| Example 19 | 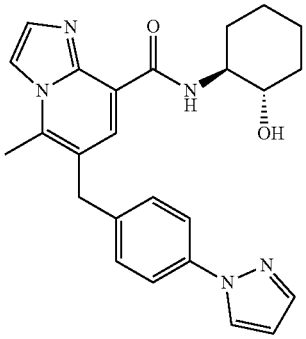 [SMILES: Cc1c(Cc2ccc(-n3cccn3)cc2)cc(C(=O)N[C@H]2CCCC[C@@H]2O)c2nccn12]<br>N-(cis-1S,2S-2-Hydroxycyclohexyl)-5-methyl-6-(4-pyrazol-1-yl-benzyl)-imidazo[1,2-a]pyridine-8-carboxamide | $^1$H-NMR (400 MHz, CDCl$_3$): δ 10.34 (d, J = 5.5 Hz, 1H), 8.18 (d, J = 7.5 Hz, 1H), 7.85 (d, J = 8.9 Hz, 1H), 7.67 (s, 2H), 7.59 (d, J = 8.8, 3H), 7.2 (d, J = 3.2 Hz, 2H), 6.81 (d, J = 7.2 Hz, 1H), 4.05 (s, 2H), 3.90 (m, 1H), 3.57 (m, 1H), 2.65 (s, 3H), 2.12 (d, 1H), 1.77-1.75 (m, 4H), 1.41-1.43 (m, 4H); Mass (m/z): 430.2 (M + H)$^+$. |
| Example 20 | 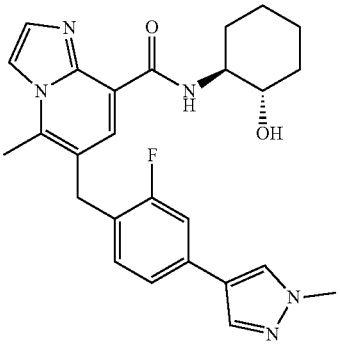<br>N-(cis-1S,2S-2-Hydroxycyclohexyl)-5-methyl-6-[2-fluoro-4-(1-methyl-1H-pyrazol-4-yl)-benzyl]-imidazo[1,2-a]pyridine-8-carboxamide | $^1$H-NMR (400 MHz, CDCl$_3$): δ 10.43 (d, J = 6.1 Hz, 1H), 8.16 (s, 1H), 7.75-7.65 (m, 2H), 7.60-7.50 (m, 2H), 7.18-7.0 (m, 2H), 7.04-6.98 (m, 1H), 4.10 (s, 2H), 4.08-3.98 (m, 1H), 3.94 (s, 3H), 3.62-3.53 (m, 1H), 2.80 (s, 3H), 2.16-2.12 (m, 2H); 1.77-1.75 (m, 2H), 1.41-1.43 (m, 4H); Mass (m/z): 462.1 (M + H)$^+$. |

| Example No. | Structure and IUPAC Name | Characterization data |
|---|---|---|
| Example 21 | 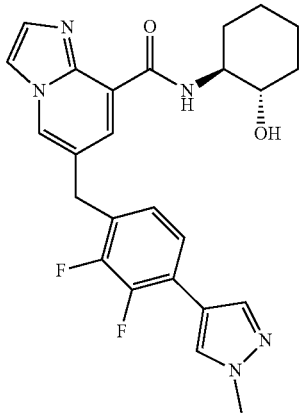 [SMILES: Cn1cc(-c2ccc(Cc3cc(C(=O)N[C@H]4CCCC[C@@H]4O)c4nccn4c3)c(F)c2F)cn1]<br>N-(cis-1S,2S-2-Hydroxycyclohexyl)-6-[2,3-difluoro-4-(1-methyl-1H-pyrazol-4-yl)-benzyl]-imidazo[1,2-a]pyridine-8-carboxamide | $^1$H-NMR (400 MHz, CDCl$_3$): δ 10.3 (bs, 1H), 8.14 (s, 1H), 8.08 (s, 1H), 7.81 (s, 1H), 7.75 (d, J = 2.0 Hz, 1H), 7.61 (d, J = 4.4 Hz, 2H), 7.27 (s, 1H), 7.0-6.96 (m, 1H), 4.05 (s, 2H), 3.96 (s, 3H), 3.95-3.89 (m, 1H), 3.6-3.5 (m, 1H), 2.13 (d, J = 12.8 Hz, 2H), 1.78 (d, J = 9.2 Hz, 2H), 1.48-1.25 (m, 4H); Mass (m/z): 466.2 (M + H)$^+$. |
| Example 22 | 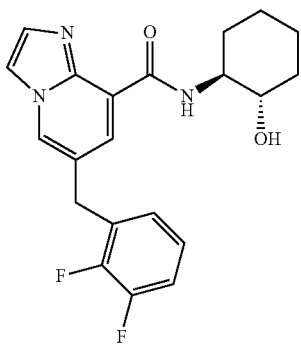 [SMILES: O=C(N[C@H]1CCCC[C@@H]1O)c1cc(Cc2cccc(F)c2F)cn2ccnc12]<br>N-(cis-1S,2S-2-Hydroxycyclohexyl)-6-(2.3-difluorobenzyl)-imidazo[1,2-a]pyridine-8-carboxamide | $^1$H-NMR (400 MHz, CDCl$_3$): δ 10.4 (bs, 1H), 8.21 (s, 1H), 8.19 (s, 1H), 7.60 (s, 1H), 7.59 (s, 1H), 7.15-6.95 (m, 3H), 4.05 (s, 2H), 3.95-3.8 (m, 2H), 3.61-3.48 (m, 1H), 2.20-2.10 (m, 2H), 1.85-1.75 (m, 2H), 1.40-1.22 (m, 4H); Mass (m/z): 386.1 (M + H)$^+$ |
| Example 23 | 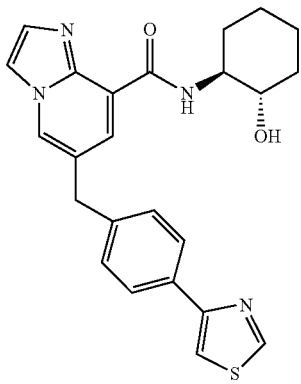 [SMILES: O=C(N[C@H]1CCCC[C@@H]1O)c1cc(Cc2ccc(-c3cscn3)cc2)cn2ccnc12]<br>N-(cis-1S,2S-2-Hydroxycyclohexyl)-6-(4-thiazol-4-yl-benzyl)-imidazo[1,2-a]pyridine-8-carboxamide | $^1$H-NMR (400 MHz, CDCl$_3$): δ 10.41 (d, J = 6.0 Hz, 1H), 8.87 (s, 1H), 8.12 (s, 1H), 7.96 (s, 1H), 7.90 (d, J = 8.0 Hz, 2H), 7.58 (s, 1H), 7.55 (s, 1H), 7.52 (s, 1H), 7.24 (d, J = 8.0 Hz, 2H), 4.06 (s, 2H), 3.93-3.90 (m, 1H), 3.6-3.58 (m, 1H), 2.14 (d, J = 10.8 Hz, 2H), 1.78 (d, J = 9.6 Hz, 2H), 1.42-1.23 (m, 4H); Mass (m/z): 433.1 (M + H)$^+$ |

| Example No. | Structure and IUPAC Name | Characterization data |
|---|---|---|
| Example 24 | 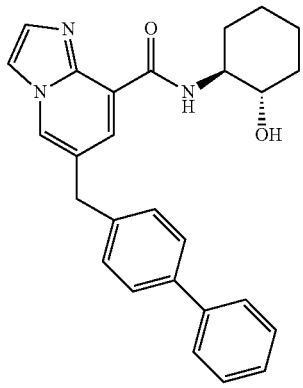 [SMILES: O=C(N[C@H]1CCCC[C@@H]1O)c1cc(Cc2ccc(-c3ccccc3)cc2)cn2ccnc12]<br>N-(cis-1S,2S-2-Hydroxycyclohexyl)-6-(4-phenyl-benzyl)-imidazo[1,2-a]pyridine-8-carboxamide | $^1$H-NMR (400 MHz, CDCl$_3$): δ 10.42 (d, J = 6.4 Hz, 1H), 8.26 (d, J = 6.4 Hz, 1H), 8.21 (d, J = 7.2 Hz, 1H), 8.12 (s, 1H), 8.00 (s, 1H), 7.65 (d, J = 6.4 Hz, 2H), 7.60-7.52 (m, 2H), 7.43 (t, J = 7.6 Hz, 2H), 7.35 (t, J = 7.2 Hz, 1H), 7.24 (d, J = 6.4 Hz, 2H), 4.05 (s, 2H), 3.93-3.85 (m, 2H), 3.62-3.57 (m, 1H), 2.17-2.11 (m, 2H), 1.79-1.77 (m, 2H), 1.58-1.33 (m, 4H); Mass (m/z): 426.2 (M + H)$^+$. |
| Example 25 | 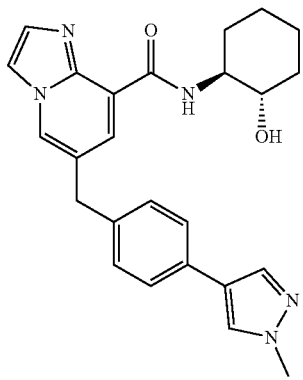 [SMILES: Cn1cc(-c2ccc(Cc3cc(C(=O)N[C@H]4CCCC[C@@H]4O)c4nccn4c3)cc2)cn1]<br>N-(cis-1S,2S-2-Hydroxycyclohexyl)-6-[4-(1-methyl-1H-pyrazol-4-yl)-benzyl]-imidazo[1,2-a]pyridine-8-carboxamide | Mass (m/z): 430.2 (M + H)$^+$ |
| Example 26 | 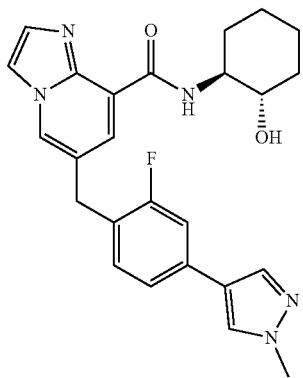 [SMILES: Cn1cc(-c2ccc(Cc3cc(C(=O)N[C@H]4CCCC[C@@H]4O)c4nccn4c3)c(F)c2)cn1]<br>N-(cis-1S,2S-2-Hydroxycyclohexyl)-6-[2-fluoro-4-(1-methyl-1H-pyrazol-4-yl)-benzyl]-imidazo[1,2-a]pyridine-8-carboxamide | Mass (m/z): 448.1 (M + H)$^+$ |

Example 27: N-(cis-1S,2S-2-Hydroxycyclohexyl)-7-methyl-6-(4-pyrazol-1-yl-benzyl)-1H-benzimidazole-4-carboxamide

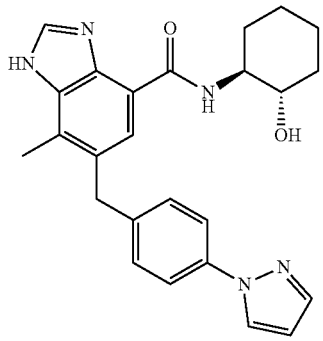 [SMILES: Cc1c(Cc2ccc(-n3cccn3)cc2)cc(C(=O)N[C@H]2CCCC[C@@H]2O)c2nc[nH]c12]

Step 1: Synthesis of ethyl 7-methyl-6-(4,4,5,5-tetramethyl-[1,3,2]dioxaborolan-2-yl)-1H-benzimidazole-4-carboxylate To a stirred solution of ethyl 6-bromo-7-methyl-1H-benzimidazole-4-carboxylate (I-12) (0.3 g, 1.06 mmol) in toluene (5.0 mL) at RT, potassium acetate (0.35 g, 3.6 mmol) and bis(pinacolato)diboron (0.4 g, 1.6 mmol) were added. Reaction mixture was degassed with nitrogen for 15 minutes and [1,1'-bis(dipherylphosphino)ferrocene]palladium(II) dichloride (86.6 mg, 0.11 mmol) was added. The reaction mixture was gradually heated to 110° C. and was stirred at this temperature for 12 h. After cooling it to RT, the reaction mass was filtered on celite and the filtrate was evaporated under reduced pressure. The crude product thus obtained was purified by silica gel column chromatography to obtain the title compound.

Yield: 0.24 g (70%); $^1$H-NMR (400 MHz, CDCl$_3$): δ 10.50 (bs, 1H), 8.35 (s, 1H), 8.11 (s, 1H), 4.49 (q, 2H), 2.98 (s, 3H), 1.44 (t, J=3.2 Hz, 3H), 1.39 (s, 12H); Mass (m/z): 331.1 (M+H)$^+$.

Step 2: Synthesis of ethyl 7-methyl-6-(4-pyrazol-1-yl-benzyl)-1H-benzimidazole-4-carboxylate Ethyl 7-methyl-6-(4,4,5,5-tetramethyl-[1,3,2]dioxaborolan-2-yl)-1H-benzimidazole—4-carboxylate obtained in step 1 (0.1 g, 0.3 mmol) was dissolved in 5:1 mixture of 1,4-dioxane and water (3.6 mL). Solid K$_2$CO$_3$ (0.06 g, 0.42 mmol) and 1-(4-chloromethyl-phenyl)-1H-pyrazole (0.06 g, 0.31 mmol) were added. The reaction mixture was degassed with nitrogen for 15 minutes and [1,1'-bis(diphenylphosphino)ferrocene]palladium(II) dichloride (24.7 mg, 0.03 mmol) was added. The reaction mixture was gradually heated to reflux temperature and was stirred at this temperature for 12 h. After cooling it to RT, the reaction mass was filtered through celite bed and the filtrate was evaporated under reduced pressure to obtain a crude product which was purified by silica gel column chromatography to obtain the title compound.

Yield: 87.0 mg (80%); $^1$H-NMR (400 MHz, CDCl$_3$): δ 10.45 (bs, 1H), 8.12 (s, 1H), 7.89-7.88 (d, J=2.2 Hz, 2H), 7.87 (s, 1H), 7.61-7.59 (d, J=6.9 Hz, 2H), 7.24 (d, J=6.5 Hz, 2H), 6.44 (s, 1H), 4.47 (q, 2H), 4.21 (s, 2H), 2.65 (s, 3H), 1.44 (t, J=7.1 Hz, 3H); (Mass (m/z): 361.1 (M+H)$^+$.

Step 3: Synthesis of 7-methyl-6-(4-pyrazol-1-yl-benzyl)-1H-benzimidazole-4-carboxylic acid To a stirred solution of ethyl 7-methyl-6-(4-pyrazol-1-yl-benzyl)-1H-benzimidazole-4-carboxylate obtained in step 2 (0.1 g, 0.28 mmol) in 1:1 mixture of H$_2$O and methanol (3.0 mL) cooled at 0° C., solid NaOH (0.022 g, 0.55 mmol) was added. After stirring for 2 h at reflux temperature, the reaction mixture was evaporated under reduced pressure to half of its volume, was cooled to RT, acidified with 1N HCl and extracted with 9:1 mixture of DCM and methanol. The combined organic layer was washed once with brine solution, dried over anhydrous Na$_2$SO$_4$ and the solvent was removed under reduced pressure to obtain the title compound.

Yield: 0.083 g (90%); $^1$H-NMR (400 MHz, DMSO: δ 15.59 (bs, 1H), 9.45 (bs, 1H), 8.45 (s, 1H), 7.91 (s, 1H), 7.91 (s, 1H), 7.77 (d, J=8.4 Hz, 2H), 7.70 (s, 1H), 7.29-7.27 (d, J=8.4 Hz, 2H), 6.51 (s, 1H), 4.24 (s, 2H), 2.66 (s, 3H); Mass (m/z): 333.1 (M+H)$^+$.

Step 4: Synthesis of N-(cis-1S,2S-2-hydroxycyclohexyl)-7-methyl-6-(4-pyrazol-1-yl-benzyl)-1H-benzimidazole-4-carboxamide To a stirred solution of 7-methyl-6-(4-pyrazol-1-yl-benzyl)-1H-benzimidazole-4-carboxylic acid obtained in step 3 (100.0 mg, 0.3 mmol) in DCM (3.0 mL) cooled at 0° C., DIPEA (0.075 mL, 0.45 mmol), cis 2-aminocyclohexanol hydrochloride (45.5 mg, 0.17 mmol) and HATU (114.0 mg, 0.3 mmol) in sequence were added. After stirring for 2 h at RT, the reaction mixture was diluted with water and DCM. The two layers were separated and aqueous layer was extracted with DCM. The combined organic layer was washed once with brine solution, dried over anhydrous Na$_2$SO$_4$ and the solvent was removed under reduced pressure to obtain a crude product which was purified by silica gel column chromatography to obtain the title compound.

Yield: 83.9 mg (65%); $^1$H-NMR (400 MHz, CDCl$_3$): δ 10.3 (bs, 1H), 9.89 (bs, 1H), 8.01 (s, 1H), 7.88 (s, 1H), 7.70 (s, 1H), 7.50-7.52 (d, J=5.36 Hz, 2H), 7.13-7.11 (d, J=6.48 Hz, 2H), 6.44 (s, 1H), 4.24 (s, 2H), 4.15 (bs, 1H), 4.03.90 (m, 1H), 3.65-3.55 (m, 1H), 3.49 (s, 3H), 2.60 (s, 3H), 2.20-2.10 (m, 2H), 1.86-1.77 (m, 2H), 1.43-1.39 (m, 4H); Mass (m/z): 430.5 (M+H)$^+$.

The following Example 28 to Example 45 were synthesized by following the experimental procedure as described in the preparation of Example 27 using the appropriate intermediates, I-9 and I-12 with some non-critical variation.

| Example No. | Structure and IUPAC name | Characterization data |
|---|---|---|
| Example 28 | 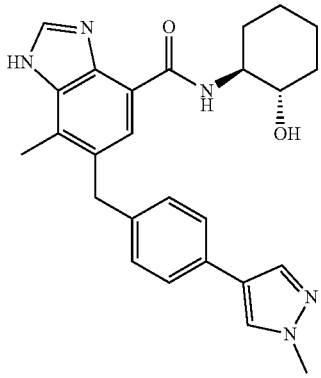 [SMILES: Cc1c(Cc2ccc(-c3cnn(C)c3)cc2)cc(C(=O)N[C@H]2CCCC[C@@H]2O)c2nc[nH]c12]<br>N-(cis-1S,2S-2-Hydroxycyclohexyl)-7-methyl-6-[4-(1-methyl-1H-pyrazol-4-yl)-benzyl]-1H-benzimidazole-4-carboxamide | $^1$H-NMR (400 MHz, CDCl$_3$): δ 10.15 (bs, 1H), 9.89 (bs, 1H), 8.04 (s, 1H), 8.03 (s, 1H), 7.69 (s, 1H), 7.52 (s, 1H), 7.3-7.29 (d, J = 7.2 Hz, 2H), 7.09-7.07 (d, J = 8.0 Hz, 2H), 4.24 (s, 2H), 3.49 (s, 3H), 3.56 (m, 2H), 2.60 (s, 3H), 2.12 (d, 1H), 1.86-1.77 (m, 4H), 1.43-1.39 (m, 4H); Mass (m/z): 444.1 (M + H)$^+$. |
| Example 29 | 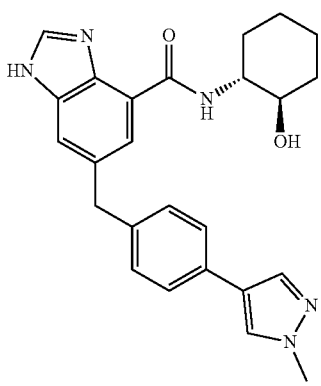 [SMILES: Cn1cc(-c2ccc(Cc3cc(C(=O)N[C@@H]4CCCC[C@H]4O)c4nc[nH]c4c3)cc2)cn1]<br>N-(cis-1S,2S-2-Hydroxycyclohexyl)-6-[4-(1-methyl-1H-pyrazol-4-yl)-benzyl]-1H-benzimidazole-4-carboxamide | $^1$H-NMR (400 MHz, CDCl$_3$): δ 9.91 (bs, 1H), 7.71 (s, 1H), 7.56 (s, 1H), 7.42 (d, J = 7.6 Hz, 2H), 7.26 (d, J = 7.6 Hz, 2H), 7.16 (s, 1H), 7.14 (s, 1H), 6.99 (s, 1H), 4.14 (s, 2H), 3.97 (s, 3H), 3.70-3.60 (m, 1H), 3.60-3.50 (m, 2H), 2.19-2.01 (m, 2H), 1.82-1.70 (m, 2H), 1.42-1.31 (m, 4H); Mass (m/z): 430.2 (M + H)$^+$. |
| Example 30 | 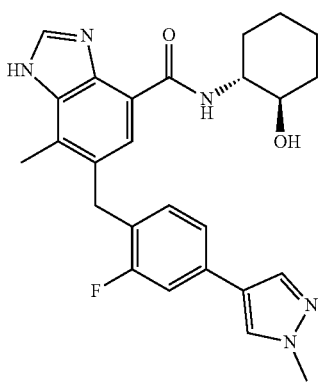 [SMILES: Cc1c(Cc2ccc(-c3cnn(C)c3)cc2F)cc(C(=O)N[C@@H]2CCCC[C@H]2O)c2nc[nH]c12]<br>N-(cis-1S,2S-2-Hydroxycyclohexyl)-7-methyl-6-[2-fluoro-4-(1-methyl-1H-pyrazol-4-yl)-benzyl]-1H-benzimidazole-4-carboxamide | $^1$H-NMR (300 MHz, CDCl$_3$): δ 8.08 (s, 1H), 7.69 (s, 1H), 7.60 (s, 1H), 7.18-7.03 (m, 4H), 6.92-6.80 (m, 2H), 4.16 (s, 2H), 3.92 (s, 3H), 3.62-3.43 (m, 2H), 2.48 (bs, 1H), 2.20-2.08 (m, 2H), 1.83-1.73 (m, 2H), 1.50-1.20 (m, 4H); Mass (m/z): 462.2 (M + H)$^+$. |

| Example No. | Structure and IUPAC name | Characterization data |
|---|---|---|
| Example 31 | 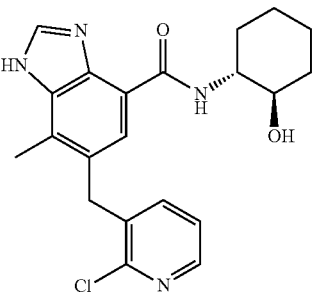 [SMILES: Cc1c(Cc2cccnc2Cl)cc(C(=O)N[C@@H]2CCCC[C@H]2O)c2nc[nH]c12]<br>N-(cis-1S,2S-2-Hydroxycyclohexyl)-7-methyl-6-[2-chloropyridin-3-ylmethyl]-1H-benzimidazole-4-carboxamide | $^1$H-NMR (400 MHz, CDCl$_3$): δ 9.84 (bs, 1H), 8.22 (s, 1H), 8.15-7.90 (m, 2H), 7.51 (s, 1H), 7.68-7.55 (m, 1H), 7.05 (s, 1H), 4.23 (s, 2H), 4.19 (bs, 1H), 4.02-3.90 (m, 1H), 3.75-3.65 (m, 1H), 2.80 (s, 3H), 2.20-2.01 (m, 2H), 1.82-1.64 (m, 2H), 1.48-1.58 (m, 4H); Mass (m/z): 399.1, 401.0 (M + H)$^+$. |
| Example 32 | 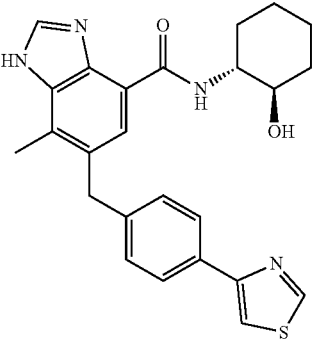 [SMILES: Cc1c(Cc2ccc(-c3cscn3)cc2)cc(C(=O)N[C@@H]2CCCC[C@H]2O)c2nc[nH]c12]<br>N-(cis-1S,2S-2-Hydroxycyclohexyl)-7-methyl-6-[4-(thiazol-4-yl)-benzyl]-1H-benzimidazole-4-carboxamide | $^1$H-NMR (400 MHz, CDCl$_3$): δ 8.85 (s, 1H), 8.60 (d, J = 3.2 Hz, 1H), 8.09 (s, 1H), 7.80 (d, J = 8.0 Hz, 2H), 7.51 (s, 2H), 7.26 (d, J = 8.0 Hz, 2H), 4.20 (s, 2H), 4.18 (bs, 1H), 3.98-3.90 (m, 1H), 3.36-3.50 (m, 1H), 2.49 (s, 3H), 2.20-2.10 (m, 2H), 1.89-1.67 (m, 2H), 1.48-1.44 (m, 2H), 1.37-1.28 (m, 2H); Mass (m/z): 447.2 (M + H)$^+$. |
| Example 33 | 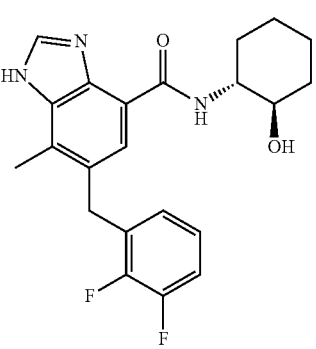 [SMILES: Cc1c(Cc2cccc(F)c2F)cc(C(=O)N[C@@H]2CCCC[C@H]2O)c2nc[nH]c12]<br>N-(cis-1S,2S-2-Hydroxycyclohexyl)-7-methyl-6-[2,3-difluorobenzyl]-1H-benzimidazole-4-carboxamide | $^1$H-NMR (400 MHz, CDCl$_3$): δ 10.02 (bs, 1H), 8.04 (s, 1H), 7.80 (dd, J = 8.0 Hz, 1H), 7.43 (dd, J = 7.2 Hz, 1H), 6.98 (dd, J = 8.0 Hz, 1H), 6.62 (s, 1H), 4.15 (s, 2H), 3.99-3.90 (m, 2H), 3.66 (bs, 1H), 2.80 (s, 3H), 2.20-2.05 (m, 2H), 1.77-1.69 (m, 2H), 1.55-1.29 (m, 4H): Mass (m/z): 400.4 (M + H)$^+$. |

| Example No. | Structure and IUPAC name | Characterization data |
|---|---|---|
| Example 34 | 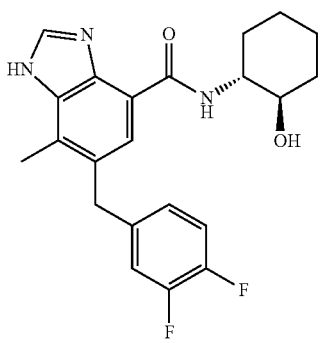 [SMILES: Cc1c(Cc2ccc(F)c(F)c2)cc(C(=O)N[C@@H]2CCCC[C@H]2O)c2nc[nH]c12]<br>N-(cis-1S,2S-2-Hydroxycyclohexyl)-7-methyl-6-[3,4-difluorobenzyl]-1H-benzimidazole-4-carboxamide | $^1$H-NMR (400 MHz, CDC$_3$): δ 8.08 (s, 1H), 7.85-7.75 (m, 1H), 7.10-7.0 (m, 2H), 6.90-6.78 (m, 2H), 4.12 (s, 2H), 4.0-3.92 (m, 2H), 3.75-3.60 (m, 1H), 2.80 (s, 3H), 2.20-2.10 (m, 2H), 1.80-1.70 (m, 2H), 1.49-1.25 (m, 4H); Mass (m/z): 400.4 (M + H)$^+$. |
| Example 35 | 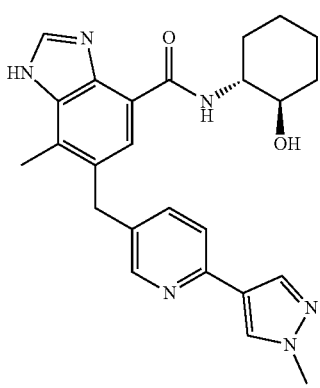 [SMILES: Cc1c(Cc2ccc(-c3cnn(C)c3)nc2)cc(C(=O)N[C@@H]2CCCC[C@H]2O)c2nc[nH]c12]<br>N-(cis-1S,2S-2-Hydroxycyclohexyl)-7-methyl-6-[6-(1-methyl-1H-pyrazol-4-yl)-pyridin-3-ylmethyl]-1H-benzimidazole-4-carboxamide | $^1$H-NMR (400 MHz, CDCl$_3$): δ 9.83 (bs, 1H), 8.38 (s, 1H), 8.07 (s, 1H), 7.89 (s, 1H), 7.86 (s, 1H), 7.31 (s, 1H), 7.30-7.25 (m, 2H), 4.15 (s, 2H), 4.0-3.90 (m, 1H), 3.93 (s, 3H), 3.65-3.49 (m, 2H), 2.41 (s, 3H), 2.15-2.05 (m, 2H), 1.85-1.75 (m, 2H), 1.44-1.40 (m, 4H); Mass (m/z): 445.2 (M + H)$^+$. |
| Example 36 | 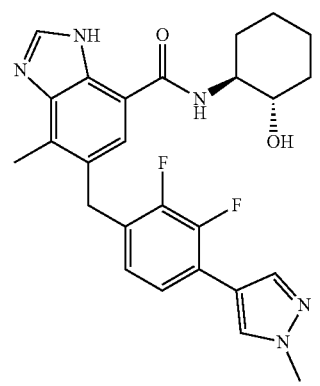 [SMILES: Cc1c(Cc2ccc(-c3cnn(C)c3)c(F)c2F)cc(C(=O)N[C@H]2CCCC[C@@H]2O)c2[nH]cnc12]<br>N-(cis-1S,2S-2-Hydroxycyclohexyl)-7-methyl-6-[2,3-difluoro-4-(1-methyl-1H-pyrazol-4-yl)-benzyl]-1H-benzimidazole-4-carboxamide | Mass (m/z): 480.2 (M + H)$^+$. |

| Example No. | Structure and IUPAC name | Characterization data |
|---|---|---|
| Example 37 | 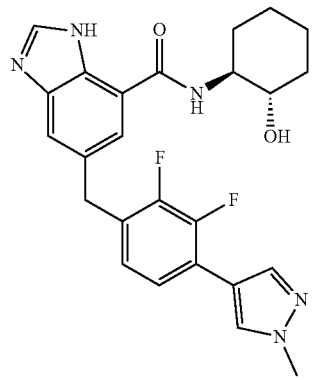 [SMILES: Cn1cc(-c2ccc(Cc3cc(C(=O)N[C@H]4CCCC[C@@H]4O)c4[nH]cnc4c3)c(F)c2F)cn1]<br>N-(cis-1S,2S-2-Hydroxycyclohexyl)-6-[2,3-difluoro-4-(1-methyl-1H-pyrazol-4-yl)-benzyl]-1H-benzimidazole-4-carboxamide | Mass (m/z): 466.1 (M + H)+. |
| Example 38 | 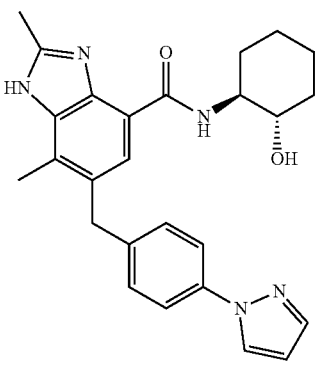 [SMILES: Cc1nc2c(C(=O)N[C@H]3CCCC[C@@H]3O)cc(Cc3ccc(-n4cccn4)cc3)c(C)c2[nH]1]<br>N-(cis-1S,2S-2-Hydroxycyclohexyl)-2,7-dimethyl-6-(4-pyrazol-1-yl-benzyl)-1H-benzimidazole-4-carboxamide | $^1$H-NMR (400 MHz, CDCl$_3$): δ 9.94 (s, 1H), 7.93 (s, 2H), 7.67 (s, 1H), 7.54 (d, J = 8.0 Hz, 2H), 7.09 (d, J = 6.5 Hz, 2H), 6.44 (s, 1H), 4.11 (s, 2H), 4.05-3.95 (m, 1H), 3.65-3.56 (m, 1H), 3.81 (s, 3H), 2.61 (s, 3H), 2.35 (s, 1H), 2.21-2.15 (m, 2H), 1.80-1.78 (m, 2H), 1.47-1.41 (m, 4H); Mass (m/z): 444.5 (M + H)+. |
| Example 39 | 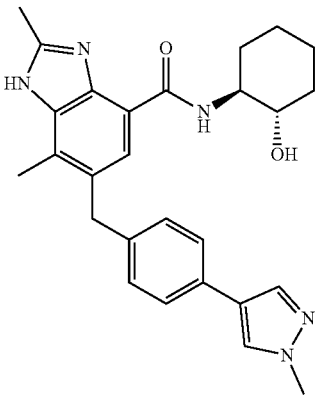 [SMILES: Cc1nc2c(C(=O)N[C@H]3CCCC[C@@H]3O)cc(Cc3ccc(-c4cnn(C)c4)cc3)c(C)c2[nH]1]<br>N-(cis-1S,2S-2-Hydroxycyclohexyl)-2,7-dimethyl-6-[4-(1-methyl-1H-pyrazol-4-yl)-benzyl]-1H-benzimidazole-4-carboxamide | $^1$H-NMR (400 MHz, CDCl$_3$): δ 9.93 (bs, 1H), 9.81 (bs, 1H), 7.89 (s, 1H), 7.76 (s, 1H), 7.49 (s, 1H), 7.24 (d, J = 4.68 Hz, 2H), 7.04 (d, J = 7.9 Hz, 2H), 3.90 (s, 2H), 3.89 (s, 3H), 3.56 (m, 2H), 2.760 (s, 6H), 2.12 (d, 1H), 1.86-1.77 (m, 4H), 1.43-1.39 (m, 4H); Mass (m/z): 458.1 (M + H)+. |

| Example No. | Structure and IUPAC name | Characterization data |
|---|---|---|
| Example 40 | 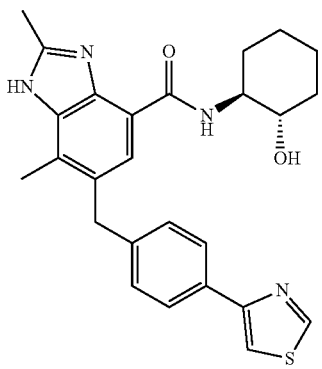 [SMILES: Cc1nc2c(C(=O)N[C@H]3CCCC[C@@H]3O)cc(Cc3ccc(-c4cscn4)cc3)c(C)c2[nH]1]<br><br>N-(cis-1S,2S-2-Hydroxycyclohexyl)-2,7-dimethyl-6-(4-thiazol-4-yl-benzyl)-1H-benzimidazole-4-carboxamide | $^1$H-NMR (400 MHz, CDCl$_3$): δ 9.95 (bs, 1H), 9.81 (bs, 1H), 8.86 (s, 1H), 7.92 (d, J = 6.1 Hz, 2H), 7.45 (s, 1H), 7.00 (d, J = 6.1 Hz, 2H), 6.96 (s, 1H), 4.11 (s, 2H), 4.05-3.95 (m, 1H), 3.65-3.55 (m, 1H), 2.81 (s, 3H), 2.63 (s, 3H), 2.2 (s, 1H), 2.18-2.10 (m, 2H), 1.80-1.77 (m, 2H), 1.47-1.44 (m, 4H); Mass (m/z): 461.2 (M + H)$^+$. |
| Example 41 | 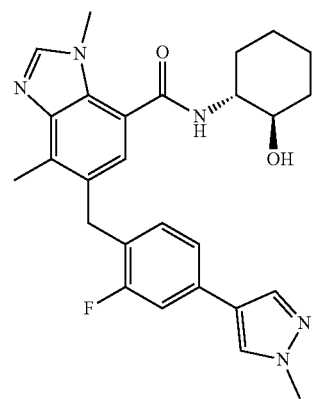 [SMILES: Cc1c(Cc2ccc(-c3cnn(C)c3)cc2F)cc(C(=O)N[C@@H]2CCCC[C@H]2O)c2c1ncn2C]<br><br>N-(cis-1S,2S-2-Hydroxycyclohexyl)-3,7-dimethyl-6-[2-fluoro-4-(1-methyl-1H-pyrazol-4-yl)-benzyl]-3H-benzimidazole-4-carboxamide | $^1$H-NMR (400 MHz, DMSO): δ 8.25 (d, J = 8.0 Hz, 1H), 8.12 (s, 2H), 7.85 (s, 1H), 7.41 (d, J = 10.8 Hz, 1H), 7.26 (d, J = 7.6 Hz, 1H), 7.19 (s, 1H), 6.94 (t, J = 8.4 Hz, 1H), 4.63 (d, J = 5.2 Hz, 1H), 4.06 (s, 2H), 3.83 (s, 6H), 3.64 (bs, 1H), 2.47 (s, 3H), 1.97-1.89 (m, 2H), 1.87-1.62 (m, 2H), 1.32-1.23 (m, 4H); Mass (m/z); 476.2.0 (M + H)$^+$. |
| Example 42 | 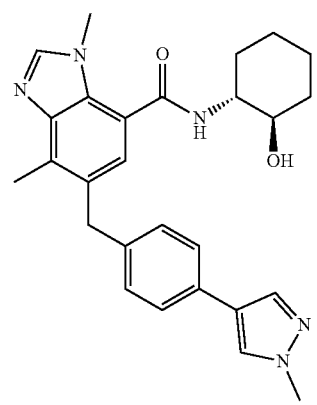 [SMILES: Cc1c(Cc2ccc(-c3cnn(C)c3)cc2)cc(C(=O)N[C@@H]2CCCC[C@H]2O)c2c1ncn2C]<br><br>N-(cis-1S,2S-2-Hydroxycyclohexyl)-3,7-dimethyl-6-[4-(1-methyl-1H-pyrazol-4-yl)-benzyl]-3H-benzimidazole-4-carboxamide | $^1$H-NMR (400 MHz, CDCl$_3$): δ 7.83 (s, 1H), 7.7 (s, 1H), 7.56 (s, 1H), 7.36 (d, J = 8.0 Hz, 2H), 7.19 (s, 1H), 7.08 (d, J = 7.6 Hz, 2H), 6.03 (d, J = 7.2 Hz, 1H), 4.14 (s, 2H), 3.92 (s, 6H), 3,3 (bs, 1H), 2.61 (s, 3H), 2.17 (s, 1H), 2.23-2.09 (m, 2H), 1.92-1.95 (m, 2H), 1.41-1.32 (m, 4H); Mass (m/z); 458.4 (M + H)$^+$. |

| Example No. | Structure and IUPAC name | Characterization data |
|---|---|---|
| Example 43 | 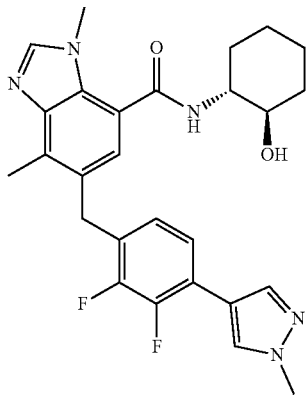 [SMILES: Cc1c(Cc2ccc(-c3cnn(C)c3)c(F)c2F)cc(C(=O)N[C@@H]2CCCC[C@H]2O)c2c1ncn2C]<br>N-(cis-1S,2S-2-Hydroxycyclohexyl)-3,7-dimethyl-6-[2,3-difluoro-4-(1-methyl-1H-pyrazol-4-yl)-benzyl]-3H-benzimidazole-4-carboxamide | $^1$H-NMR (400 MHz, CDCl$_3$): δ 7.84 (s, 1H), 7.78 (s, 1H), 7.74 (d, J = 2.0 Hz, 1H), 7.0 (s, 1H), 7.12-7.08 (m, 1H), 6.63-6.61 (m, 1H), 6.05 (d, J = 7.2 Hz, 1H), 4.14 (s, 2H), 3.95 (s, 3H), 3.92 (s, 3H), 3.90-3.85 (m, 1H), 3.73-3.63 (m, 1H), 3.29 (d, J = 4.4 Hz, 1H), 2.61 (s, 3H), 2.16-2.08 (m, 2H), 1.82-1.75 (m, 2H), 1.45-1.20 (m, 4H); Mass (m/z): 494.3 (M + H)$^+$. |
| Example 44 | 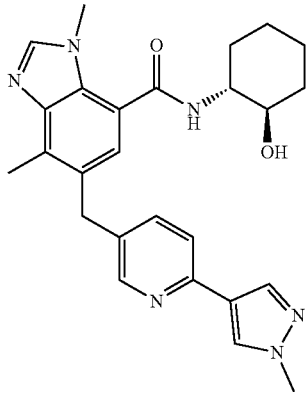 [SMILES: Cc1c(Cc2ccc(-c3cnn(C)c3)nc2)cc(C(=O)N[C@@H]2CCCC[C@H]2O)c2c1ncn2C]<br>N-(cis-1S,2S-2-Hydroxycyclohexyl)-3,7-dimethyl-6-[6-(1-methyl-1H-pyrazol-4-yl)-pyridin-3-ylmethyl]-3H-benzimidazole-4-carboxamide | $^1$H-NMR (400 MHz, CDCl$_3$): δ 9.96 (d, J = 5.2 Hz, 1H), 8.38 (s, 1H), 8.06 (s, 1H), 7.99 (s, 1H), 7.89 (s, 1H), 7.76 (s, 1H), 7.43-7.32 (m, 2H), 4.17 (s, 2H), 4.08 (s, 3H), 4.0-3.90 (m, 1H), 3.94 (s, 3H), 3.75-3.58 (m, 1H), 2.61 (s, 3H), 2.20-2.10 (m, 2H), 2.04 (bs, 1H), 1.78-1.70 (m, 2H), 1.32-1.25 (m, 4H); Mass (m/z): 459.2 (M + H)$^+$. |
| Example 45 | 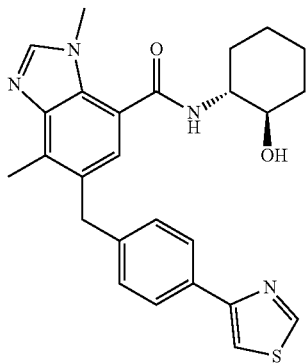 [SMILES: Cc1c(Cc2ccc(-c3cscn3)cc2)cc(C(=O)N[C@@H]2CCCC[C@H]2O)c2c1ncn2C]<br>N-(cis-1S,2S-2-Hydroxycyclohexyl)-3,7-dimethyl-6-[4-(thiazol-4-yl)-benzyl]-3H-benzimidazole-4-carboxamide | $^1$H-NMR (400 MHz, CDCl$_3$): δ 8.86 (s, 1H), 8.75 (0d, J = 4.0 Hz, 1H), 8.29 (s, 1H), 7.9-7.8 (m, 2H), 7.49-7.44 (m, 2H), 7.23 (s, 2H), 4.28 (s, 2H), 4.20 (bs, 1H), 4.06 (s, 3H), 3.73 (bs, 1H), 2.80 (s, 3H), 2.67-2.55 (m, 4H), 1.3-1.24 (m, 2H), 0.97-0.86 (m, 2H); Mass (m/z): 461.2 (M + H)$^+$. |

Example 46: N-(cis-1S,2S-2-Hydroxycyclohexyl)-2,4-dimethyl-5-[4-(1-methyl-1H-pyrazol-4-yl)-benzyl]-benzofuran-7-carboxamide

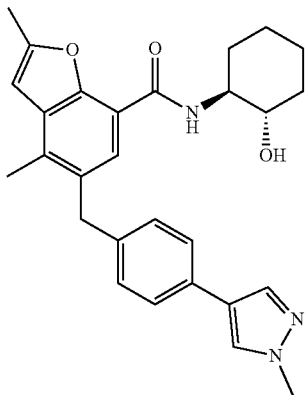 [SMILES: Cc1cc2c(C)c(Cc3ccc(-c4cnn(C)c4)cc3)cc(C(=O)N[C@H]3CCCC[C@@H]3O)c2o1]

Step 1: Methyl 2,4-dimethyl-5-[4-(1-methyl-1H-pyrazol-4-yl)-benzyl]-benzofuran-7-carboxylate To a stirred solution of methyl 5-bromo-2,4-dimethyl-benzofuran-7-carboxylate (I-21) (0.1 g, 0.35 mmol) in toluene (3.5 mL) at RT, potassium acetate (0.106 g, 1.43 mmol) and bis(pinacolato)diboron (0.13 g, 0.53 mmol) were added. The reaction mixture was degassed with nitrogen for 15 minutes and [1,1'-bis(diphenylphosphino)ferrocene] palladium(II) dichloride (43.0 mg, 0.053 mmol) was added. The reaction mixture was gradually heated to 100° C. and was stirred at this temperature for 20 h. After cooling it to RT, the crude product in toluene was diluted with 9:1 mixture of 1,4-dioxane and water (3.7 mL). Solid $K_2CO_3$ (0.06 g, 0.42 mmol) and 4-(4-chloromethyl-phenyl)-1-methyl-1H-pyrazole (0.06 g, 0.30 mmol) were added. The reaction mixture was degassed with nitrogen for 15 minutes and [1,1'-bis(diphenylphosphino)ferrocene] palladium(II) dichloride (25.0 mg, 0.03 mmol) was added. The reaction mixture was gradually heated to 100° C. and was stirred at this temperature for 6 h. After cooling it to RT, the volatiles were removed under reduced pressure and the crude product was dissolved in water and EtOAc. The reaction mass was filtered through celite bed and the two layers were separated. The aqueous layer was extracted with EtOAc. The combined organic layer was washed once with brine solution, dried over anhydrous $Na_2SO_4$ and the solvent was removed under reduced pressure to obtain a crude product which was purified by silica gel column chromatography to obtain the title compound.

Yield: 0.59 mg (52%); $^1$H-NMR (400 MHz, $CDCl_3$): δ 7.72 (d, J=7.6 Hz, 2H), 7.55 (s, 1H), 7.36 (d, J=8.1 Hz, 2H), 7.10 (d, J=8.0 Hz, 2H), 6.41 (s, 1H), 4.11 (s, 2H), 3.97 (s, 3H), 3.92 (s, 3H), 2.52 (s, 3H), 2.37 (s, 3H); Mass (m/z): 375.0 (M+H)$^+$.

Step 2: 2,4-Dimethyl-5-[4-(1-methyl-1H-pyrazol-4-yl)-benzyl]-benzofuran-7-carboxylic acid To a stirred solution of methyl 2,4-dimethyl-5-[4-(1-methyl-1H-pyrazol-4-yl)-benzyl]-benzofuran-7-carboxylate (0.06 g, 0.16 mmol) in 1:1 mixture of $H_2O$ and methanol (0.6 mL) cooled at 0° C., solid NaOH (0.013 g, 0.31 mmol) was added. After stirring for 2 h at reflux temperature, the reaction mixture was cooled to RT, acidified with 2N HCl and extracted with DCM. The combined organic layer was washed once with brine solution, dried over anhydrous $Na_2SO_4$ and the solvent was removed under reduced pressure to obtain the title compound as an off white solid.

Yield: 0.045 g (80%); $^1$H-NMR (400 MHz, DMSO): δ 13.8 (bs, 1H), 8.06 (s, 1H), 7.81 (s, 1H), 7.56 (s, 1H), 7.46 (d, J=8.04 Hz, 2H), 7.11 (d, J=8.0 Hz, 2H), 6.71 (s, 1H), 4.05 (s, 2H), 3.85 (s, 3H), 2.46 (s, 3H), 2.39 (s, 3H); Mass (m/z): 360.9 (M+H)$^+$.

Step 3: N-(cis-1S,2S-2-Hydroxycyclohexyl)-2,4-dimethyl-5-[4-(1-methyl-1H-pyrazol-4-yl)-benzyl]-benzofuran-7-carboxamide To a stirred solution of 2,4-dimethyl-5-[4-(1-methyl-1H-pyrazol-4-yl)-benzyl]-benzofuran-7-carboxylic acid (45.0 mg, 0.12 mmol) in DCM (0.5 mL) cooled at 0° C., DIPEA (0.05 mL, 0.31 mmol), cis 2-aminocyclohexanol hydrochloride (19.0 mg, 0.12 mmol) and HATU (52.3 mg, 0.14 mmol) in sequence were added. After stirring for 2 hour at RT, the reaction mixture was diluted with water and DCM. The two layers were separated and aqueous layer was extracted with DCM. The combined organic layer was washed once with brine solution, dried over anhydrous $Na_2SO_4$ and the solvent was removed under reduced pressure to obtain a crude product which was purified by silica gel column chromatography to obtain the title compound.

Yield: 21.1 mg (36%); $^1$H-NMR (400 MHz, $CDCl_3$): δ 7.8 (s, 1H), 7.70 (s, 1H), 7.52 (s, 1H), 7.39 (d, J=8.16 Hz, 2H), 7.10 (d, J=7.96 Hz, 2H), 6.46 (s, 1H), 4.15 (s, 2H), 3.97 (m, 3H), 3.92 (s, 3H), 3.56-3.49 (m, 1H), 2.51 (s, 3H), 2.35 (s, 3H), 2.16-2.12 (m, 2H), 1.80-1.77 (m, 2H), 1.49-1.38 (m, 4H); Mass (m/z): 458.0 (M+H)$^+$.

Example 47

Determination of allosteric potency $EC_{50}$ values for Muscarinic M1 receptor:

A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with $EC_{20}$ of acetylcholine in OptiMEM medium to the cells. The incubation was continued at 37° C. in $CO_2$ incubator for 4 h. Medium was removed and cells were washed with phosphate buffered saline. The cells were lysed and luciferase activity was measured in a Luminometer. Luminescence counts in each concentrations of test item were normalized to the acetylcholine induced maximum response and the data was analyzed using Graphpad software. $EC_{50}$ values of the compounds were defined as the concentration required in stimulating the luciferase activity by 50% in presence of $EC_{20}$ of acetylcholine.

| Example No. | EC$_{50}$ (nM) |
|---|---|
| 1 | 719 |
| 2 | 1681 |
| 3 | 1237 |
| 4 | 960 |
| 5 | 2341 |
| 6 | 1668 |
| 7 | 232 |
| 8 | 168 |
| 9 | 185 |
| 10 | 157 |
| 11 | 100 |
| 12 | 258 |
| 13 | 249 |
| 14 | 555 |
| 15 | 197 |
| 16 | 798 |
| 17 | 1116 |
| 18 | 248 |
| 19 | 178 |
| 20 | 28 |
| 21 | 1046 |
| 22 | 3822 |
| 23 | 308 |
| 24 | 3908 |
| 25 | 444 |
| 26 | 3338 |
| 27 | 357 |
| 28 | 105 |
| 29 | 449 |
| 30 | 151 |
| 31 | 2816 |
| 32 | 516 |
| 33 | 3660 |
| 34 | 2283 |
| 35 | 237 |
| 36 | 465 |
| 37 | 597 |
| 38 | 694 |
| 39 | 895 |
| 40 | 1498 |
| 41 | 1063 |
| 42 | 10000 |

-continued

| Example No. | EC$_{50}$ (nM) |
|---|---|
| 43 | 1460 |
| 44 | 208 |
| 45 | 10000 |
| 46 | 299 |

Example 48

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (i.v) (1 mg/kg) dosing (n=3/group) and fasted overnight before oral dosing (p.o.). However, rats allocated to intravenous (i.v.) dosing food and water was provided ad libitum.

At pre-determined point, blood was collected through jugular vein and replenished with an equivalent volume of normal saline. Collected blood was transferred into a labelled eppendorf tube containing 10 μL of heparin as an anticoagulant. Typically blood samples were collected at following time points: 0.08, 0.25, 0.5, 1, 2, 4, 6, 8, and 24 h post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters $C_{max}$, $T_{max}$ (h), $AUC_t$, $T_{1/2}$, clearance and bioavailability (F) were calculated by non-compartmental model using standard non-compartmental model by using Phoenix WinNonlin 6.0.2 or 6.0.3 version Software package.

| Example No. | ROA | $C_{max}$ (ng/mL) | $T_{max}$ (hr) | AUC$_{0-t}$ (ng·hr/mL) | $t_{1/2}$ (h) | Clearance (mL/min/kg) | F (%) |
|---|---|---|---|---|---|---|---|
| 1 | oral | 150 ± 39 | 0.50-1.0 | 360 ± 117 | 1.1 ± 0.1 | — | 24 ± 8 |
|   | i.v. | — | — | 492 ± 22 | 1.3 ± 0.5 | 34 ± 1.5 |   |
| 2 | oral | 48 ± 23 | 0.50-2.0 | 158 ± 58 | 2.0 ± 0.2 | — | 14 ± 5 |
|   | i.v. | — | — | 367 ± 39 | 1.6 ± 0.3 | 45 ± 5 |   |
| 6 | oral | 582 ± 72 | 0.5 | 1001 ± 38 | 1.3 ± 0.2 | — | 50 ± 2 |
|   | i.v. | — | — | 664 ± 81 | 1.5 ± 0.6 | 25 ± 3.3 |   |
| 8 | oral | 2327 ± 441 | 2 | 18400 | 3.6 ± 0.2 | — | 100 ± 16 |
|   | i.v. | — | — | 6147 ± 485 | 3.3 ± 0.7 | 2.7 ± 0.2 |   |
| 11 | oral | 9693 ± 1415 | 1.0-2.0 | 40300 ± 9418 | 4.8 ± 1.6 | — | 105 ± 25 |
|   | i.v. | — | — | 12767 ± 2146 | 3.9 ± 0.2 | 1.3 ± 0.2 |   |
| 14 | oral | 70 ± 23 | 0.5 | 137 ± 28 | 1.9 ± 0.1 | — | 13 ± 2.7 |
|   | i.v. | — | — | 346 ± 25 | 0.8 ± 0.1 | 48 ± 3.4 |   |
| 15 | oral | 1540 ± 397 | 2.0 | 8187 ± 2176 | 3.7 ± 0.3 | — | 40 ± 11 |
|   | i.v. | — | — | 6857 ± 1806 | 3.1 ± 0.3 | 2.5 ± 0.6 |   |
| 17 | oral | 288 ± 26.5 | 1 | 705 ± 118 | 1.3 ± 0.1 | — | 37 ± 6 |
|   | i.v. | — | — | 635 ± 70 | 1.3 ± 0.2 | 26 ± 3 |   |

Example 49

Rodent Brain Penetration Study

Male Wistar rats (260±40 grams) were used as experimental animals. Three animals were housed in each cage. Animals were given water and food ad libitum throughout the experiment and maintained on a 12 h light/dark cycle.

Brain penetration was determined in discrete manner in rats. One day prior to dosing day, male Wistar rats were acclimatized and randomly grouped according to their weight. At each time point (0.5, 1 and 2 h) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$) and the results are tabulated below.

| Example No. | Single dose Rat Brain Penetration ($C_b/C_p$) at 3 mg/kg, p.o. @ 1.0 hr |
|---|---|
| 1 | 0.54 ± 0.04 |
| 2 | 1.74 ± 0.03 |
| 6 | 0.26 ± 0.04 |
| 11 | 0.14 ± 0.01 |
| 14 | 1.27 ± 0.07 |
| 15 | 0.78 ± 0.22 |
| 17 | 0.32 ± 0.06 |

Example 50

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 h light/dark cycle in temperature and humidity controlled room. The experiment was carried out in circular arena made up of acrylic. Rats were habituated to individual arenas for up to 45 min in the absence of any objects on day 1.

One group of 12 rats received vehicle and another set of animals received compound of the formula (I), before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 h after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects (a1+a2).

$T_2$ is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

| | | Exploration time mean ± S.E.M (sec) | | |
|---|---|---|---|---|
| Example Number | Dose | Familiar object | Novel object | Inference |
| 11 | 0.3 mg/kg, p.o. | 12.20 ± 1.89 | 17.33 ± 1.39 | Active |
| 14 | 3 mg/kg, p.o. | 8.35 ± 1.98 | 15.54 ± 3.58 | Active |
| 15 | 1 mg/kg, p.o. | 12.93 ± 1.83 | 20.42 ± 3.42 | Active |

Example 51

Evaluation of Theta Modulation in Dorsal Hippocampus of Anesthetized Male Wistar Rats in Combination with Acetylcholine Esterase Inhibitor Donepezil.

Effect of Example 11 in combination with donepezil on brain activity as a pharmacodynamic endpoint is evaluated.

Male Wistar rats (240-320 g) were anesthetized by intraperitoneal administration of urethane (1.2 to 1.5 g/kg) for implantation of a catheter in the left femoral vein. The animal was placed in a stereotaxic frame for implanting an electrode (stainless steel wire, Plastics One) into the dorsal hippocampus (AP: −3.8 mm; ML: +2.2 mm; DV: −2.5 mm; Paxinos and Watson, 2004). Bipolar stimulating electrode (untwisted stainless steel wires, separated by 0.75-1.0 mm at their tips, Plastics One) was implanted in the Nucleus Pontis Oralis (NPO; AP: −7.8 mm; ML: 1.8 mm; DV: −6.0 mm; Paxinos and Watson, 2004). Additionally one electrode was implanted into the cerebellum which served as a reference. Hippocampal θ rhythm was evoked via a 6-s electrical stimulation train (20-160 PA, 0.3-ms pulse duration, 250 Hz) delivered to the NPO at a rate of 0.01 trains/s with a Grass S88 stimulator and PSIU6 stimulus isolation unit (Grass Medical Instruments, Quincy, Mass.). EEG was recorded at a rate of 1000 Hz using Ponemah (Version 5.2) software and stored for off-line analysis using NeuroScore (Version 3.0). Baseline amplitude level was achieved by using the current required to elicit θ rhythm to 50% of the maximal amplitude under control conditions. After the stabilization period of one hour, baseline recording was done for 30 min followed by the treatment of vehicle or Example 11 (1 mg/kg, i.v.). Donepezil (0.3 mg/kg, i.v.) was administered 30 min after Example 11 treatment and recording was continued for additional 1 hour.

Statistical Analysis:

Power in the θ rhythm frequency in the stimulation period during the 30 min baseline period was calculated and the % changes in these measures post treatment were calculated. The percent change in relative theta power after combination of Example 11 and donepezil was compared with donepezil using two-way analysis of variance (time and treatment), followed by Bonferroni's posttest. Statistical significance was considered at a p value less than 0.05.

REFERENCE

1. Paxinos G. and Watson C. (2004) Rat brain in stereotaxic coordinates. Academic Press, New York.

Results:

Treatment with donepezil produced moderate increase in hippocampal θ power. Example 11 in combination with donepezil produced significant increase in θ power levels. The effect in combination treatment was observed to be significantly higher than the donepezil alone (FIG. 1).

Mean area under the curve values (AUC) calculated after the treatment of Example 11 and donepezil was significantly higher compared to donepezil alone treatment (FIG. 1).

We claim:

1. A compound of formula (I),

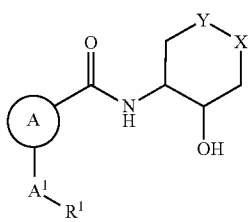

wherein:

$R^1$ is —($C_{6-10}$)-aryl or —($C_{5-10}$)-heteroaryl; each of which is optionally substituted with one or more substituents selected from halogen, —OH, —O—($C_{1-6}$)-alkyl, —S—($C_{1-6}$)-alkyl, —N(CH$_3$)$_2$, —($C_{1-6}$)-alkyl, —($C_{3-6}$)-cycloalkyl, halo($C_{1-6}$)-alkyl, —NH$_2$, —CN and $R^{1a}$;

$R^{1a}$ is —($C_{6-10}$)-aryl or —($C_{5-10}$)-heteroaryl; each of which is optionally substituted with one or more substituents selected from the group consisting of halogen, —OH, —NH$_2$, —CN, —O—($C_{1-6}$)-alkyl, —S—($C_{1-6}$)-alkyl, —($C_{1-6}$)-alkyl and —($C_{3-6}$)-cycloalkyl;

$A^1$ is CH$_2$ or CHF;

ring A is selected from the group consisting of:

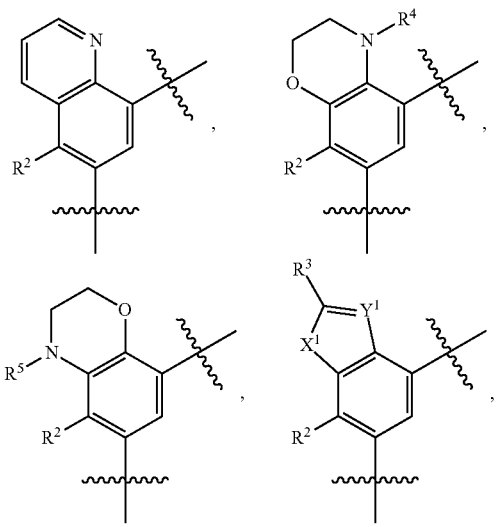

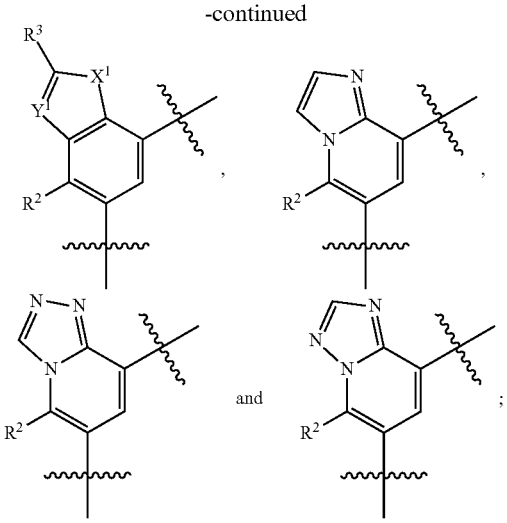

"⁓⁓⁓" represents point of attachment;

$R^2$ is hydrogen, —($C_{1-6}$)-alkyl or —($C_{3-6}$)-cycloalkyl;

$R^3$ is hydrogen, halogen, —OH, —($C_{1-6}$)-alkyl, —O—($C_{1-6}$)-alkyl or halo($C_{1-6}$)-alkyl;

$R^4$ is hydrogen, —($C_{1-6}$)-alkyl or halo($C_{1-6}$)-alkyl;

$R^5$ is hydrogen, —($C_{1-6}$)-alkyl or halo($C_{1-6}$)-alkyl;

$X^1$ is independently selected from O, S, NH or NCH$_3$;

$Y^1$ is independently selected from N or CH;

X is independently selected from CH$_2$, O, NH or NCH$_3$; and

Y is independently selected from CH$_2$, O, NH or NCH$_3$;

or an isotopic form, a stereoisomer, a tautomer or a pharmaceutically acceptable salt thereof.

2. The compound of formula (I) as claimed in claim 1, wherein:

ring A is selected from the group consisting of;

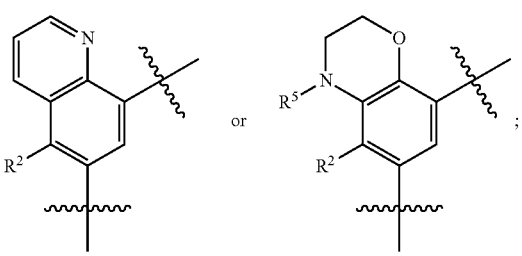

$R^1$ is —($C_{6-10}$)-aryl or —($C_{5-10}$)-heteroaryl; each of which is optionally substituted with one or more substituents selected from halogen and $R^{1a}$;

$R^{1a}$ is —($C_{5-10}$)-heteroaryl; which is optionally substituted with —($C_{1-6}$)-alkyl;

$A^1$ is CH$_2$;

"⁓⁓⁓" represents point of attachment;

$R^2$ is hydrogenor-($C_{1-6}$)-alkyl;

$R^5$ is hydrogen;

X is independently selected from CH$_2$ or O; and

Y is CH$_2$;

or an isotopic form, a stereoisomer, a tautomer or a pharmaceutically acceptable salt thereof.

3. The compound of formula (I) as claimed in claim 1, wherein:
ring A is selected from the group consisting of;

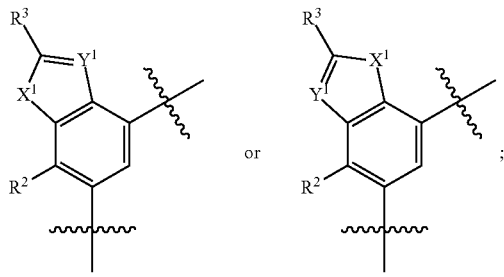

R¹ is —(C$_{6-10}$)-aryl or —(C$_{5-10}$)-heteroaryl; each of which is optionally substituted with one or more substituents selected from halogen and R$^{1a}$;
R$^{1a}$ is —(C$_{5-10}$)-heteroaryl; which is optionally substituted with —(C$_{1-6}$)-alkyl;
A¹ is CH$_2$;
"⌇⌇⌇⌇" represents point of attachment;
R² is hydrogen or —(C$_{1-6}$)-alkyl;
R³ is hydrogen, or —(C$_{1-6}$)-alkyl;
X¹ is independently selected from O, or NH;
Y¹ is independently selected from N or CH;
X is CH$_2$; and
Y is CH$_2$;
or an isotopic form, a stereoisomer, a tautomer or a pharmaceutically acceptable salt thereof.

4. The compound of formula (I) as claimed in claim 1, wherein:
ring A is

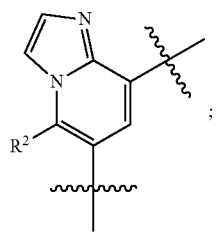

R¹ is —(C$_{6-10}$)-aryl; which is optionally substituted with one or more substituents selected from halogen, and R$^{1a}$;
R$^{1a}$ is —(C$_{6-10}$)-aryl or —(C$_{5-10}$)-heteroaryl; each of which is optionally substituted with —(C$_{1-6}$)-alkyl;
A¹ is CH$_2$;
"⌇⌇⌇⌇" represents point of attachment;
R² is hydrogen or —(C$_{1-6}$)-alkyl;
X is CH$_2$;
Y is CH$_2$;
or an isotopic form, a stereoisomer, a tautomer or a pharmaceutically acceptable salt thereof.

5. The compound as claimed in claim 1, wherein the compound is selected from the group consisting of:
N-(cis-1S,2S-2-Hydroxycyclohexyl)-6-(2-chloropyridin-4-ylmethyl)-5-methylquinoline-8-carboxamide;
N-(cis-1S,2S-2-Hydroxycyclohexyl)-6-(2,3-difluorobenzyl)-5-methylquinoline-8-carboxamide;
N-(cis-3S,4S-3-Hydroxytetrahydropyran-4-yl)-6-(2-chloropyridin-5-ylmethyl)-5-methylquinoline-8-carboxamide;
N-(cis-1S,2S-2-Hydroxycyclohexyl)-6-(2-fluoropyridin-4-ylmethyl)-5-methylquinoline-8-carboxamide;
N-(cis-1S,2S-2-Hydroxycyclohexyl)-6-(2-fluorobenzyl)-5-methylquinoline-8-carboxamide;
N-(cis-1S,2S-2-Hydroxycyclohexyl)-6-(2-chloropyridin-5-ylmethyl)-5-methylquinoline-8-carboxamide;
N-(cis-1S,2S-2-Hydroxycyclohexyl)-6-[2-(1-methyl-1H-pyrazol-4-yl)-pyridin-5-ylmethyl]-5-methylquinoline-8-carboxamide;
N-(cis-1S,2S-2-Hydroxycyclohexyl)-6-[2,3-difluoro-4-(1-methyl-1H-pyrazol-4-yl)-benzyl]-5-methylquinoline-8-carboxamide;
N-(cis-1S,2S-2-Hydroxycyclohexyl)-6-[3-fluoro-4-(1-methyl-1H-pyrazol-4-yl)-benzyl]-5-methylquinoline-8-carboxamide;
N-(cis-1S,2S-2-Hydroxycyclohexyl)-6-(4-pyrazol-1-yl-benzyl)-5-methylquinoline-8-carboxamide;
N-(cis-1S,2S-2-Hydroxycyclohexyl)-6-[2-fluoro-4-(1-methyl-1H-pyrazol-4-yl)-benzyl]-5-methylquinoline-8-carboxamide;
N-(cis-1S,2S-2-Hydroxycyclohexyl)-6-(4-thiazol-4-yl-benzyl)-5-methylquinoline-8-carboxamide;
N-(cis-3S,4S-3-Hydroxytetrahydropyran-4-yl)-6-(4-thiazol-4-yl-benzyl)-5-methylquinoline-8-carboxamide;
N-(cis-1S,2S-2-Hydroxycyclohexyl)-6-benzyl-5-methylquinoline-8-carboxamide;
N-(cis-1S,2S-2-Hydroxycyclohexyl)-6-[4-(1-methyl-1H-pyrazol-4-yl)-benzyl]-5-methylquinoline-8-carboxamide;
N-(cis-1S,2S-2-Hydroxycyclohexyl)-6-[4-(1-methyl-1H-pyrazol-4-yl)-benzyl]-5-methyl-3,4-dihydro-2H-benzo[1,4]oxazine-8-carboxamide;
N-(cis-1S,2S-2-Hydroxycyclohexyl)-6-(4-pyrazol-1-yl-benzyl)-5-methyl-3,4-dihydro-2H-benzo[1,4]oxazine-8-carboxamide;
N-(cis-1S,2S-2-Hydroxycyclohexyl)-5-methyl-6-[4-(1-methyl-1H-pyrazol-4-yl)-benzyl]-imidazo[1,2-a]pyridine-8-carboxamide;
N-(cis-1S,2S-2-Hydroxycyclohexyl)-5-methyl-6-(4-pyrazol-1-yl-benzyl)-imidazo[1,2-a]pyridine-8-carboxamide;
N-(cis-1S,2S-2-Hydroxycyclohexyl)-5-methyl-6-[2-fluoro-4-(1-methyl-1H-pyrazol-4-yl)-benzyl]-imidazo[1,2-a]pyridine-8-carboxamide;
N-(cis-1S,2S-2-Hydroxycyclohexyl)-6-[2,3-difluoro-4-(1-methyl-1H-pyrazol-4-yl)-benzyl]-imidazo[1,2-a]pyridine-8-carboxamide;
N-(cis-1S,2S-2-Hydroxycyclohexyl)-6-(2,3-difluorobenzyl)-imidazo[1,2-a]pyridine-8-carboxamide;
N-(cis-1S,2S-2-Hydroxycyclohexyl)-6-(4-thiazol-4-yl-benzyl)-imidazo[1,2-a]pyridine-8-carboxamide;
N-(cis-1S,2S-2-Hydroxycyclohexyl)-6-(4-phenyl-benzyl)-imidazo[1,2-a]pyridine-8-carboxamide;
N-(cis-1S,2S-2-Hydroxycyclohexyl)-6-[4-(1-methyl-1H-pyrazol-4-yl)-benzyl]-imidazo[1,2-a]pyridine-8-carboxamide;
N-(cis-1S,2S-2-Hydroxycyclohexyl)-6-[2-fluoro-4-(1-methyl-1H-pyrazol-4-yl)-benzyl]-imidazo[1,2-a]pyridine-8-carboxamide;
N-(cis-1S,2S-2-Hydroxycyclohexyl)-7-methyl-6-(4-pyrazol-1-yl-benzyl)-1H-benzimidazole-4-carboxamide;
N-(cis-1S,2S-2-Hydroxycyclohexyl)-7-methyl-6-[4-(1-methyl-1H-pyrazol-4-yl)-benzyl]-1H-benzimidazole-4-carboxamide;

N-(cis-1S,2S-2-Hydroxycyclohexyl)-6-[4-(1-methyl-1H-pyrazol-4-yl)-benzyl]-1H-benzimidazole-4-carboxamide;

N-(cis-1S,2S-2-Hydroxycyclohexyl)-7-methyl-6-[2-fluoro-4-(1-methyl-1H-pyrazol-4-yl)-benzyl]-1H-benzimidazole-4-carboxamide;

N-(cis-1S,2S-2-Hydroxycyclohexyl)-7-methyl-6-[2-chloropyridin-3-ylmethyl]-1H-benzimidazole-4-carboxamide;

N-(cis-1S,2S-2-Hydroxycyclohexyl)-7-methyl-6-[4-(thiazol-4-yl)-benzyl]-1H-benzimidazole-4-carboxamide;

N-(cis-1S,2S-2-Hydroxycyclohexyl)-7-methyl-6-[2,3-difluorobenzyl]-1H-benzimidazole-4-carboxamide;

N-(cis-1S,2S-2-Hydroxycyclohexyl)-7-methyl-6-[3,4-difluorobenzyl]-1H-benzimidazole-4-carboxamide;

N-(cis-1S,2S-2-Hydroxycyclohexyl)-7-methyl-6-[6-(1-methyl-1H-pyrazol-4-yl)-pyridin-3-ylmethyl]-1H-benzimidazole-4-carboxamide;

N-(cis-1S,2S-2-Hydroxycyclohexyl)-7-methyl-6-[2,3-difluoro-4-(1-methyl-1H-pyrazol-4-yl)-benzyl]-1H-benzimidazole-4-carboxamide;

N-(cis-1S,2S-2-Hydroxycyclohexyl)-6-[2,3-difluoro-4-(1-methyl-1H-pyrazol-4-yl)-benzyl]-1H-benzimidazole-4-carboxamide;

N-(cis-1S,2S-2-Hydroxycyclohexyl)-2,7-dimethyl-6-(4-pyrazol-1-yl-benzyl)-1H-benzimidazole-4-carboxamide;

N-(cis-1S,2S-2-Hydroxycyclohexyl)-2,7-dimethyl-6-[4-(1-methyl-1H-pyrazol-4-yl)-benzyl]-1H-benzimidazole-4-carboxamide;

N-(cis-1S,2S-2-Hydroxycyclohexyl)-2,7-dimethyl-6-(4-thiazol-4-yl-benzyl)-1H-benzimidazole-4-carboxamide;

N-(cis-1S,2S-2-Hydroxycyclohexyl)-3,7-dimethyl-6-[2-fluoro-4-(1-methyl-1H-pyrazol-4-yl)-benzyl]-3H-benzimidazole-4-carboxamide;

N-(cis-1S,2S-2-Hydroxycyclohexyl)-3,7-dimethyl-6-[4-(1-methyl-1H-pyrazol-4-yl)-benzyl]-3H-benzimidazole-4-carboxamide;

N-(cis-1S,2S-2-Hydroxycyclohexyl)-3,7-dimethyl-6-[2,3-difluoro-4-(1-methyl-1H-pyrazol-4-yl)-benzyl]-3H-benzimidazole-4-carboxamide;

N-(cis-1S,2S-2-Hydroxycyclohexyl)-3,7-dimethyl-6-[6-(1-methyl-1H-pyrazol-4-yl)-pyridin-3-ylmethyl]-3H-benzimidazole-4-carboxamide;

N-(cis-1S,2S-2-Hydroxycyclohexyl)-3,7-dimethyl-6-[4-(thiazol-4-yl)-benzyl]-3H-benzimidazole-4-carboxamide; and N-(cis-1S,2S-2-Hydroxycyclohexyl)-2,4-dimethyl-5-[4-(1-methyl-1H-pyrazol-4-yl)-benzyl]-benzofuran-7-carboxamide;

or a pharmaceutically acceptable salt thereof.

6. A pharmaceutical composition comprising the compound of formula (I) or a pharmaceutically acceptable salt thereof as claimed in claim 1 and pharmaceutically acceptable excipients.

7. The pharmaceutical composition as claimed in claim 6, for the treatment of disease or disorder mediated by muscarinic M1 receptor, wherein said disease or disorder is selected from the group consisting of cognitive disorders, Alzheimer's disease, schizophrenia, pain or sleep disorders.

8. A method of treatment of disease or disorder mediated by muscarinic M1 receptor, wherein the disease or disorder is selected from the group consisting of cognitive disorders, Alzheimer's disease, schizophrenia, pain or sleep disorders comprising administering to a patient in need thereof, a therapeutically effective amount of the compound of formula (I) or a pharmaceutically acceptable salt thereof as claimed in claim 1.

9. The method of treating disease or disorder as claimed in claim 8, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

10. A combination comprising the compound of formula (I) as claimed in claim 1, with one or more therapeutic agents selected from acetylcholinesterase inhibitors and NMDA receptor antagonist.

11. The combination as claimed in claim 10, wherein the acetylcholinesterase inhibitor is selected from the group consisting of donepezil, rivastigmine, tacrine and galantamine or a pharmaceutically acceptable salt thereof, and the NMDA receptor antagonist is memantine or a pharmaceutically acceptable salt thereof.

12. A method of treating disease or disorder mediated by muscarinic M1 receptor, wherein the disease or disorder mediated by muscarinic M1 receptor is selected from cognitive disorders, Alzheimer's disease, schizophrenia, pain or sleep disorders, comprising administering to a patient in need thereof, a therapeutically effective amount of the combination as claimed in claim 10.

13. A pharmaceutical composition comprising the compound of formula (I) or a pharmaceutically acceptable salt thereof as claimed in claim 5 and pharmaceutically acceptable excipients.

14. The pharmaceutical composition as claimed in claim 13, for the treatment of disease or disorder mediated by muscarinic M1 receptor, wherein said disease or disorder is selected from the group consisting of cognitive disorders, Alzheimer's disease, schizophrenia, pain or sleep disorders.

15. A method of treatment of disease or disorder mediated by muscarinic M1 receptor, wherein the disease or disorder is selected from the group consisting of cognitive disorders, Alzheimer's disease, schizophrenia, pain or sleep disorders comprising administering to a patient in need thereof, a therapeutically effective amount of the compound of formula (I) or a pharmaceutically acceptable salt thereof as claimed in claim 5.

16. The method of treating disease or disorder as claimed in claim 15, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

17. A combination comprising the compound of formula (I) as claimed in claim 5, with one or more therapeutic agents selected from acetylcholinesterase inhibitors and NMDA receptor antagonist.

18. The combination as claimed in claim 17, wherein the acetylcholinesterase inhibitor is selected from the group consisting of donepezil, rivastigmine, tacrine and galantamine or a pharmaceutically acceptable salt thereof and the NMDA receptor antagonist is memantine or a pharmaceutically acceptable salt thereof.

19. A method of treating disease or disorder mediated by muscarinic M1 receptor, wherein the disease or disorder mediated by muscarinic M1 receptor is selected from cognitive disorders, Alzheimer's disease, schizophrenia, pain or sleep disorders, comprising administering to a patient in need thereof, a therapeutically effective amount of the combination as claimed in claim 17.

* * * * *